United States Patent
Coulter

(10) Patent No.: US 9,387,179 B2
(45) Date of Patent: Jul. 12, 2016

(54) PHARMACEUTICAL CYCLOSPORIN COMPOSITIONS

(71) Applicant: Sigmoid Pharma Limited, Dublin (IE)

(72) Inventor: Ivan Coulter, Dublin (IE)

(73) Assignee: Sigmoid Pharma Limited, Dublin (IE)

( * ) Notice: Subject to any disclaimer, the term of this patent is extended or adjusted under 35 U.S.C. 154(b) by 0 days.

(21) Appl. No.: 13/942,492

(22) Filed: Jul. 15, 2013

(65) Prior Publication Data

US 2013/0330411 A1  Dec. 12, 2013

Related U.S. Application Data

(62) Division of application No. 12/594,534, filed as application No. PCT/IE2008/000038 on Apr. 4, 2008, now Pat. No. 8,535,713.

(60) Provisional application No. 61/006,498, filed on Jan. 16, 2008, provisional application No. 60/907,490, filed on Apr. 4, 2007.

(51) Int. Cl.
| | |
|---|---|
| *A61K 9/50* | (2006.01) |
| *A61K 31/436* | (2006.01) |
| *A61K 38/13* | (2006.01) |
| *A61K 9/00* | (2006.01) |
| *A61K 45/06* | (2006.01) |
| *A61K 31/439* | (2006.01) |
| *A61K 31/635* | (2006.01) |
| *A61K 38/28* | (2006.01) |
| *A61K 39/00* | (2006.01) |

(52) U.S. Cl.
CPC ............ *A61K 9/5073* (2013.01); *A61K 9/0053* (2013.01); *A61K 9/50* (2013.01); *A61K 9/5015* (2013.01); *A61K 9/5026* (2013.01); *A61K 9/5042* (2013.01); *A61K 9/5047* (2013.01); *A61K 9/5057* (2013.01); *A61K 9/5089* (2013.01); *A61K 31/436* (2013.01); *A61K 31/439* (2013.01); *A61K 31/635* (2013.01); *A61K 38/13* (2013.01); *A61K 38/28* (2013.01); *A61K 39/0005* (2013.01); *A61K 45/06* (2013.01); *A61K 2039/55583* (2013.01)

(58) Field of Classification Search
CPC . A61K 9/0053; A61K 9/5015; A61K 9/5057; A61K 9/5073; A61K 9/5026; A61K 9/5047; A61K 9/50; A61K 31/436; A61K 38/13; A61K 45/06

See application file for complete search history.

(56) References Cited

U.S. PATENT DOCUMENTS

| | | |
|---|---|---|
| 4,279,632 A | 7/1981 | Frosch et al. |
| 4,379,454 A | 4/1983 | Campbell et al. |
| 4,388,307 A | 6/1983 | Cavanak |
| 4,422,985 A | 12/1983 | Morishita et al. |
| 4,460,563 A | 7/1984 | Calanchi |
| 4,481,157 A | 11/1984 | Morishita et al. |
| 4,597,959 A | 7/1986 | Barr |
| 4,601,894 A | 7/1986 | Hanna et al. |
| 4,652,441 A | 3/1987 | Okada et al. |
| 4,656,161 A | 4/1987 | Herr |
| 4,695,466 A | 9/1987 | Morishita et al. |
| 4,748,023 A | 5/1988 | Tamás et al. |
| 4,749,574 A | 6/1988 | Ueda et al. |
| 4,751,241 A | 6/1988 | Motoyama et al. |
| 4,857,335 A | 8/1989 | Bohm |
| 5,102,668 A | 4/1992 | Eichel et al. |
| 5,145,684 A | 9/1992 | Liversidge et al. |
| 5,330,835 A | 7/1994 | Kikuchi et al. |
| 5,342,625 A | 8/1994 | Hauer et al. |
| 5,362,564 A | 11/1994 | Suzuki et al. |
| 5,385,737 A | 1/1995 | Shigeno et al. |
| 5,411,952 A | 5/1995 | Kaswan |
| 5,478,508 A | 12/1995 | Suzuki et al. |
| 5,480,655 A | 1/1996 | Jizomoto et al. |
| 5,492,701 A | 2/1996 | Cervos et al. |
| 5,500,224 A | 3/1996 | Vranckx et al. |
| 5,510,118 A | 4/1996 | Bosch et al. |
| 5,529,783 A | 6/1996 | Burke et al. |
| 5,571,533 A | 11/1996 | Santus et al. |
| 5,645,856 A | 7/1997 | Lacy et al. |
| 5,650,232 A | 7/1997 | Glenn et al. |
| 5,665,386 A | 9/1997 | Benet et al. |
| 5,674,495 A | 10/1997 | Bowersock et al. |
| 5,795,590 A | 8/1998 | Kiefer et al. |
| 5,827,531 A | 10/1998 | Morrison et al. |
| 5,843,347 A | 12/1998 | Nguyen et al. |

(Continued)

FOREIGN PATENT DOCUMENTS

| | | |
|---|---|---|
| AU | 1977031116 | 12/1976 |
| AU | 627220 B2 | 8/1992 |

(Continued)

OTHER PUBLICATIONS

S.N.S Murthy, et al, Treatment of Dextran Sulfate Sodium-Induced Murine Colitis by Intracolonic Cyclosporine, 38 Dig. Disease Sci. 1722 (1993).*

(Continued)

*Primary Examiner* — Sean Basquill
(74) *Attorney, Agent, or Firm* — Klarquist Sparkman, LLP

(57) ABSTRACT

An oral cyclosporin composition comprises minicapsules having a core containing a cyclosporin, especially cyclosporin A in a solubilized liquid form. The minicapsules have a release profile to release the pre-solubilized cyclosporin, at least in the colon. The composition may be used for treating a range of intestinal diseases [FIG. 10].

44 Claims, 7 Drawing Sheets

(56) References Cited

U.S. PATENT DOCUMENTS

| | | | |
|---|---|---|---|
| 5,851,275 A | 12/1998 | Amidon et al. | |
| 5,858,401 A | 1/1999 | Bhalani et al. | |
| 5,871,774 A | 2/1999 | Lemelson | |
| 5,882,680 A * | 3/1999 | Suzuki et al. | 424/451 |
| 5,958,876 A | 9/1999 | Woo et al. | |
| 5,961,970 A | 10/1999 | Lowell et al. | |
| 6,022,562 A | 2/2000 | Autant et al. | |
| 6,113,936 A | 9/2000 | Takebayashi et al. | |
| 6,146,663 A | 11/2000 | Bissery et al. | |
| 6,174,466 B1 | 1/2001 | Kiefer et al. | |
| 6,190,692 B1 | 2/2001 | Busetti et al. | |
| 6,204,243 B1 * | 3/2001 | Posanski | 424/408 |
| 6,251,661 B1 | 6/2001 | Urabe et al. | |
| 6,267,985 B1 | 7/2001 | Chen et al. | |
| 6,284,271 B1 | 9/2001 | Lundberg et al. | |
| 6,309,663 B1 | 10/2001 | Patel et al. | |
| 6,361,298 B1 | 3/2002 | Kiefer et al. | |
| 6,429,089 B1 | 8/2002 | Matsuki | |
| 6,457,339 B2 | 10/2002 | Komura | |
| 6,531,150 B1 | 3/2003 | Sunohara et al. | |
| 6,569,463 B2 | 5/2003 | Patel et al. | |
| 6,585,997 B2 | 7/2003 | Moro et al. | |
| 6,620,788 B1 | 9/2003 | Tanida et al. | |
| 6,761,903 B2 | 7/2004 | Chen et al. | |
| 6,923,988 B2 | 8/2005 | Patel et al. | |
| 6,972,132 B1 | 12/2005 | Kudo et al. | |
| 7,267,813 B2 | 9/2007 | Watanabe et al. | |
| 7,374,779 B2 | 5/2008 | Chen et al. | |
| 8,535,713 B2 * | 9/2013 | Coulter | 424/452 |
| 2001/0003589 A1 | 6/2001 | Neuer et al. | |
| 2001/0024658 A1 | 9/2001 | Chen et al. | |
| 2002/0009457 A1 | 1/2002 | Bowersock et al. | |
| 2002/0098242 A1 | 7/2002 | Darder | |
| 2003/0045516 A1 | 3/2003 | Luly et al. | |
| 2003/0055028 A1 | 3/2003 | Stergiopoulos et al. | |
| 2003/0078194 A1 | 4/2003 | Cho et al. | |
| 2003/0104048 A1 | 6/2003 | Patel et al. | |
| 2003/0124061 A1 | 7/2003 | Roberts | |
| 2003/0180352 A1 | 9/2003 | Patel et al. | |
| 2003/0193102 A1 | 10/2003 | Yan | |
| 2003/0232076 A1 | 12/2003 | Makino et al. | |
| 2003/0235595 A1 | 12/2003 | Chen et al. | |
| 2004/0028619 A1 | 2/2004 | Watanabe et al. | |
| 2004/0029855 A1 | 2/2004 | Klaveness et al. | |
| 2004/0062802 A1 | 4/2004 | Hermelin | |
| 2004/0126428 A1 | 7/2004 | Hughes et al. | |
| 2004/0230183 A1 | 11/2004 | Breegi et al. | |
| 2004/0258701 A1 | 12/2004 | Dominowski et al. | |
| 2005/0037077 A1 | 2/2005 | Legrand et al. | |
| 2005/0095288 A1 | 5/2005 | Honea | |
| 2005/0249807 A1 | 11/2005 | Brown et al. | |
| 2006/0018965 A1 | 1/2006 | Moodley et al. | |
| 2006/0034937 A1 | 2/2006 | Patel | |
| 2006/0135441 A1 | 6/2006 | Khodadoust et al. | |
| 2006/0222701 A1 | 10/2006 | Kulkarni et al. | |
| 2007/0154554 A1 | 7/2007 | Burgermeister et al. | |
| 2007/0292523 A1 | 12/2007 | Moodley et al. | |
| 2008/0020018 A1 | 1/2008 | Moodley et al. | |
| 2008/0107694 A1 | 5/2008 | Trogden et al. | |
| 2008/0113031 A1 | 5/2008 | Moodley et al. | |
| 2008/0124279 A1 | 5/2008 | Andremont et al. | |
| 2008/0311201 A1 | 12/2008 | Der-Yang et al. | |
| 2008/0318912 A1 | 12/2008 | Fox et al. | |
| 2010/0136105 A1 | 6/2010 | Chen et al. | |
| 2010/0215737 A1 | 8/2010 | Coulter | |
| 2010/0239665 A1 | 9/2010 | Coulter | |
| 2010/0255087 A1 * | 10/2010 | Coulter | 424/457 |
| 2010/0297221 A1 | 11/2010 | Coulter | |

FOREIGN PATENT DOCUMENTS

| | | | |
|---|---|---|---|
| CA | 2170748 | 3/1995 | |
| CA | 2376261 | 6/2000 | |
| CN | 1557283 | 12/2004 | |
| DE | 198 48 849 A1 | 10/1998 | |
| EP | 0 348 910 | 6/1989 | |
| EP | 0 396 425 | 11/1990 | |
| EP | 0 525 731 | 2/1993 | |
| EP | 0 550 067 | 7/1993 | |
| EP | 0 621 775 | 11/1994 | |
| EP | 0 650 721 | 5/1995 | |
| EP | 0 760 237 | 3/1997 | |
| EP | 0 778 083 | 6/1997 | |
| EP | 0 922 451 | 6/1999 | |
| EP | 0 813 876 | 3/2002 | |
| EP | 0813876 * | 3/2002 | A61K 9/48 |
| EP | 0 789 561 | 4/2004 | |
| EP | 1 811 979 | 11/2008 | |
| GB | 2257359 | 1/1993 | |
| JP | A-58 013508 | 1/1983 | |
| JP | A-58 077810 | 5/1983 | |
| JP | 59-088420 | 5/1984 | |
| JP | A-61 151119 | 7/1986 | |
| JP | 64-000015 | 1/1989 | |
| JP | H0549899 A | 3/1993 | |
| JP | 7247215 A | 9/1995 | |
| JP | 2000-247911 | 9/2000 | |
| JP | 2000-302654 | 10/2000 | |
| JP | 64 000015 | 8/2010 | |
| WO | WO 93/00063 | 1/1993 | |
| WO | WO 94/15636 | 7/1994 | |
| WO | WO 96/36322 | 11/1996 | |
| WO | WO 97/02017 | 1/1997 | |
| WO | WO 97/02042 | 1/1997 | |
| WO | WO 97/25980 | 7/1997 | |
| WO | WO 98/18610 | 5/1998 | |
| WO | WO 98/50018 | 11/1998 | |
| WO | WO 98/50033 | 11/1998 | |
| WO | WO 99/06024 | 2/1999 | |
| WO | WO 99/13914 | 3/1999 | |
| WO | WO 00/00179 | 1/2000 | |
| WO | WO 00/33862 | 6/2000 | |
| WO | WO 00/69420 | 11/2000 | |
| WO | WO 01/32142 | 5/2001 | |
| WO | WO 01/37808 | 5/2001 | |
| WO | WO 01/51008 | 7/2001 | |
| WO | WO 01/80831 | 11/2001 | |
| WO | WO 03/018134 | 3/2003 | |
| WO | WO 03/020243 | 3/2003 | |
| WO | WO 03/030878 | 4/2003 | |
| WO | WO 03/053404 | 7/2003 | |
| WO | WO 03/056938 | 7/2003 | |
| WO | WO 03/068196 | 8/2003 | |
| WO | WO 03/092741 | 11/2003 | |
| WO | WO 2004/022220 | 3/2004 | |
| WO | WO 2004/042024 | 5/2004 | |
| WO | WO 2004/052339 | 6/2004 | |
| WO | WO 2004/064997 | 8/2004 | |
| WO | WO 2004/084870 | 10/2004 | |
| WO | WO 2004/108121 | 12/2004 | |
| WO | WO 2005/020993 | 3/2005 | |
| WO | WO 2005/020994 | 3/2005 | |
| WO | WO 2005/030205 | 4/2005 | |
| WO | WO 2005/048998 | 6/2005 | |
| WO | WO 2005/072088 | 8/2005 | |
| WO | WO 2005/074913 | 8/2005 | |
| WO | WO 2005/100454 | 10/2005 | |
| WO | WO 2005/107721 | 11/2005 | |
| WO | WO 2006/026592 | 3/2006 | |
| WO | WO2006/035416 * | 4/2006 | A61K 9/50 |
| WO | WO 2006/035416 | 4/2006 | |
| WO | WO 2006/110802 | 10/2006 | |
| WO | WO 2007/012478 | 2/2007 | |
| WO | WO 2007/014445 | 2/2007 | |
| WO | WO 2007/018943 | 2/2007 | |
| WO | WO 2007/095092 | 8/2007 | |
| WO | WO 2009/002533 | 12/2008 | |

OTHER PUBLICATIONS

Snezana Milojevic, et al, Amylose as a Coating for Drug Delivery to the Colon: Preparation and In Vitro Evaluation Using 5-aminosalicylic Acid Pellets, 38 J Control. Rel. 75 (1996).*

(56) References Cited

OTHER PUBLICATIONS

William Sandborn, et al, The Pharmacokinetic and Colonic Tissue Concentrations of Cyclosporine After IV, Oral, and Enema Administration, 31 J Clin. Pharmacol. 76 (1991.*

J.E. Riviere, et al, Effects of Vasoactive Drugs on Transdermal Lidocaine Iontophoresis, 80 J Pharma. Sci. 615 (1991).*

Laurent Loufrani & Daniel Henrion, Vasodilator Treatment with Hydralazine Increases Blood Flow in mdx Mice Resistance Arteries Without Vascular Wall Remodelling or Endothelium Function Impairment, 23 J Hyperten. 1855 (2005).*

Sandborn et al. "The Pharmacokinetics and Colonic Tissue Concentration of Cyclosporine After IV, Oral, and Enema Administration," *J. Clin. Pharrncicol.* 31: 76-80, 1991.

Watts et al. "Colonic Drug Delivery," *Drug Development and Industrial Pharmacy*, 23(9): 893-913, 1997.

Dhara et al., "Stability of Sodium Dodecyl Sulfate Micelles in the Presence of a Range of Water-Soluble Polymers: A Pressure-Jump Study," *J. Phys. Chem. B.*, 105: 7133-7138; 2001.

Greener et al., "Interaction of Anionic Surfactants with Gelatin: Viscosity Effects," *Macromolecules*, 20: 2490-2498; 1987.

Holmberg et al., *Surfactants and Polymers in Aqueous Solution*. John Wiley & Sons, Ltd. 2002.

Muller et al. "Competitive Adssorption of Gelatin and Sodium Dodecylbenzenesulfonate at Hydrophobic Surfaces," *Langmuir*, 14: 3107-3114; 1998.

Wesley et al., "Structure of Polymer/Surfactant Complexes Formed by Poly(2- (dimethylamino)ethyl metharylate) and Sodium Dodecyl Sulfate," *Langmuir* 18: 5704-5707; 2002.

Akhlaghi et al., "Distribution of Cyclosporin in Organ Transplant Recipients," *Clin Pharmacokinet* 41(9):615-637, 2002.

Al-Meshal et al., "Oral administration of liposomes containing cyclosporine: a pharmacokinetic study," *International Journal of Pharmaceutics* 168:163-168, 1998.

Anderberg et al., "Sodium Caprate Elicits Dilatations in Human Intestinal Tight Junctions and Enhances Drug Absorption by the Paracellular Route," *Pharmaceutical Research* 10(6):857-864, 1993.

Barnes et al., "Theophylline: New Perspectives for an Old Drug," *Am J Respir Crit Care Med* 167:813-818, 2003.

Borel et al., "Carotenoids in biological emulsions: solubility, surface-to-core distribution, and release from lipid droplets," *Journal of Lipid Research* 37:250-261, 1996.

Cannon, "Oral Solid Dosage Forms of Lipid-based Drug Delivery Systems," *AM Pharm Rev* 8(1):108-115, 2005.

Chourasia et al., "Pharmaceutical approaches to colon targeted drug delivery systems," *J. Pharm. Pharmaceut. Sci.* 6(1):33/66/2003.

Chowdary et al., "Controlled Nifedipine Release from Microcapsules of its Dispersions in PVP-MCC and HPC-MCC," *Drug Development and Industrial Pharmacy* 21(10):1183-1192, 1995.

Cummins et al., "The Hydroxylase Inhibitor Dimethyloxalylglycine is Protective in a Murine Model of Colitis," *Gastroenterology* 134:156-165, 2008.

Drewe et al., "The absorption site of cyclosporine in the human gastro-intestinal tract," *Br. J. clin. Pharmac.* 33:39-43, 1992.

Feagan et al., "Low-Dose Cyclosporine for the Treatment of Crohn's Disease," *The New England Journal of Medicine*, 330(26):1846-1851, Jun. 30, 1994.

French et al., "Evaluation of the Physiochemical Properties and Dissolution Characteristics of Mesalamine: Relevance to Controlled Intestinal Drug Delivery," *Pharmaceutical Research* 10(9):1285-1290, 1993.

Gao et al., "Physiochemical characterization and evaluation of a microemulsion system for oral delivery of cyclosporin A," *International Journal of Pharmaceutics* 161:75-86, 1998.

Gursoy et al., "Self-emulsifying drug delivery systems (SEDDS) for improved oral delivery of lipophilic drugs," *Biomedicine & Pharmacotherapy* 58:173-182, 2004.

Ikegawa et al., Inhibition of P-glycoprotein by flavonoid derivatives in Adriamycin-resistant human myelogenous leukemia (K562/ADM)cells, *Cancer Letters* 177:89-93, 2002.

Ismailos et al., "Unusual solubility behavior of cyclosporin A in aqueous media," *J. Pharm. Pharmacol.* 43:28-289, 1990.

Kim et al., "Once-a-Day Oral Dosing Regimen of Cyclosporin A: Combined Therapy of Cyclosporin A Premicroemulsion Concentrates and Enteric Coated Solid-State Premicroemulsion Concentrates," *Pharmaceutical Research* 18(4):454-459, 2001.

Klausner et al., "Expandable gastroretentive dosage forms," *Journal of Controlled Release* 90:143-162, 2003.

Liu et al., "Gelatin-Stabilised Microemulsion-Based Organogels Facilitates Percutaneous Penetration of Cyclosporin A In Vitro and Dermal Pharmacokinetics In Vivo," *Journal of Pharmaceutical Sciences* 96(11):3000-3009, Nov. 2007.

Loufrani et al., "Vasodilator treatment with hydralazine increases blood flow in mdx mice resistance arteries without vacular wall remodeling or endothelium function improvement," *Journal of Hypertension* 23:1855-1860, 2005.

Madene et al., "Flavour encapsulation and controlled release—a review," *International Journal of Food Science and Technology* 41:1-21, 2006.

Manakova et al., "Failure of FK506 (tacrolimus) to alleviate apomorphine-induced circling in rat Parkinson model in spite of some cytoprotective effects in SH-SY5Y dopaminergic cells," *Brain Research* 1038:83-91, 2005.

McGinity et al., "Enteric Film Coating of Soft Gelatin Capsules," *Drug Development & Delivery* 3(6), Sep. 6, 2003.

McGinity et al., Aqueous Polymeric Coatings for Pharmaceuticals Dosage Forms, *Marcel Dekker, Inc.*, 1997.

Miller et al., "Controlled Trial of Nimodipine in Amyotrophic Lateral Sclerosis," *Neuromusc. Disord.*, 6(2):101-104, 1996.

Milojevic et al., "Amylose as a coating for drug delivery to the colon: Preparation and in vitro evaluation using 5-aminosalicylic acid pellets," *Journal of Controlled Release* 38:75-84, 1996.

Murthy et al., "Treatment of Dextran Sulfate Sodium-Induced Murine Colitis by Intracolonic Cyclosporin," *Digestive Diseases and Sciences* 38(9):1722-1734, Sep. 1993.

Qiu et al., "Developing Solid Oral Dosage Forms: Pharmaceutical Theory & Practice," *Academic Press* p. 445 only, 2009.

Reich, "Formulation and physical properties of soft capsules," *Chapter 11, Pharmaceutical Capsules*, $2^{nd}$ edition, Edited by Fridrun Podczeck and Brian E Jones, p. 208, 2004.

Ribeiro et al., "Microencapsulation of lipophilic drugs in chitosan-coated alginate microspheres," *International Journal of Pharmaceutics* 187:115-123, 1999.

Riviere et al., "Effects of Vasoactive Drugs on Transdermal Lidocaine Iontophoresis," *Journal of Pharmaceutical Sciences* 80(7):615-620, Jul. 1991.

Rodriguez et al., "Colonic budesonide delivery from ph-dependent microcapsules containing lipidic cores," *Acta Technologiae et Legis Medicamenti* 11(1):45-52, 2000.

Strowig et al., Comparison of Insulin Monotherapy and Combination Therapy with Insulin and Metformin or Insulin and Troglitazone in Type 2 Diabetes, *Diabetes Care* 25(10):1691-1698, 2002.

Sweetman and Martindale, "Nimodipine," *Cardiovascular Drugs* p. 946, 2002.

van Deventer, "Small therapeutic molecules for the treatment of inflammatory bowel disease," *Gut* 50(Suppl III):iii47-iii53, 2002.

Yang et al., "Transport and uptake characteristics of a new derivative of berberine (CPU-86017) by human intestinal epithelial cell line: Caco-2," *Acta Pharmacol Sin* 24(12):1185-1191, 2003.

Yeh et al., "Effect of Medium-Chain Glycerides on Physiological Properties of Rabbit Intestinal Epithelium in Vitro," *Pharmaceutical Research* 11(8):1148-1154, 1994.

Zhang et al., "P-glycoprotein restricted transport of nimodipine across blood-brain barrier," *Acta Pharmacol Sin* 24(9):903-906, 2003.

Zuber et al., "Reversible cerebral angiopathy," *J. Neurol* 253:1585-1588, 2006.

Drug Bank, www.drugbank.ca/drugs/DB00244, 12 pages.

Non-Final Office Action from U.S. Appl. No. 11/236,549 dated May 5, 2009.

Non-Final Office Action from U.S. Appl. No. 11/663,834 dated Mar. 3, 2010.

(56) References Cited

OTHER PUBLICATIONS

Non-Final Office Action from U.S. Appl. No. 11/236,549 dated Oct. 6, 2010.
Final Office Action from U.S. Appl. No. 11/663,834 dated Jun. 17, 2011.
Final Office action from U.S. Appl. No. 11/236,549, dated Mar. 15, 2012.
Non-final Office action from U.S. Appl. No. 12/598,395, dated Mar. 26, 2012.
Non-Final Office Action from U.S. Appl. No. 12/597,154 dated Jun. 21, 2012.
Final Office Action from U.S. Appl. No. 12/594,553 dated Sep. 10, 2012.
Non-Final Office Action from U.S. Appl. No. 12/594,542 dated Oct. 5, 2012.
Non-Final Office Action from U.S. Appl. No. 13/321,149 dated Nov. 9, 2012.
Non-Final Office Action from U.S. Appl. No. 13/441,780 dated Nov. 28, 2012.

Shioji, Yusaku "Manufacturing technology of solid formulation", CMC Publishing Co. Ltd., pp. 46-48 and 174-177, Jan. 27, 2003.
Office action issued for Japanese Patent Application No. 2006-507572.
Rutgeerts et al., "A comparison of Budesonide with Prednisolone for Active Crohn's Disease," *The New England journal of Medicine*, 331(13): 842-845, 1994.
Wakerly et al., "Pectin/Ethylcellulose Film Coating Formulations for Colonic Drug Delivery," Pharmaceutical Research, 13(8): 1210-1212, 1996.
Asghar et al., "Multiparticulate Formulation Approach to Colon Specific Drug Delivery: Current Perspectives," *J. Pharm. Pharmaceut. Sci.*, 9(3): 327-338, Nov. 16, 2006.
Homar et al., "Influence of polymers on the bioavailability of microencapsulated celecoxib," *Journal of Microencapsulation*, 24(7): 621-633, Nov. 2007.
Tang et al., "Coating of Multiparticulates for Sustained Release," *Am. J. Drug Deliv.*, 3(1): 17-28, Mar. 2005.

\* cited by examiner

PHARMACEUTICAL CYCLOSPORIN COMPOSITIONS

CROSS-REFERENCE TO RELATED APPLICATIONS

This is a divisional of U.S. application Ser. No. 12/594,534, which was filed on Feb. 22, 2010, which is the U.S. National Stage of International Application No. PCT/IE2008/000038, filed Apr. 4, 2008, which was published in English under PCT Article 21(2), which in turn claims the benefit of U.S. Provisional Application No. 60/907,490, filed Apr. 4, 2007, and U.S. Provisional Application No. 61/006,498, filed Jan. 16, 2008. The applications are incorporated herein in their entirety.

The present invention relates to pharmaceutical cyclosporin compositions.

INTRODUCTION

Cyclosporins form a class of polypeptides commonly possessing immunosuppressive and anti-inflammatory activity. The most commonly known cyclosporin is cyclosporin-A. Other forms of cyclosporins include cyclosporin-B, -C, -D, and -G and their derivatives. It should be understood that herein the terms "cyclosporin" or "cyclosporins" refers as used herein to any of the several cyclosporins derivatives or prodrugs thereof, or to any mixture of any of the above.

Cyclosporin A is a hydrophobic material exhibiting poor bioavailability. To improve the aqueous solubility of the hydrophobic cyclosporin A, the current marketed liquid oral formulations are emulsified using a mixture of oils, ethanol, a triglyceride and a surfactant (U.S. Pat. No. 4,388,307). While overcoming the solubility problem, these formulations have a variety of difficulties, such as unpleasant taste, which is unacceptable for long-term therapy. Therefore, the use of soft gelatin capsule dosage forms masks the taste of the solution as well as unitising the dose.

The bioavailability of these liquid formulations or the soft gelatin capsule formulation containing ethanol, oils and Labrafil surfactant, is low and variable, and reported to be about 30%. U.S. Pat. No. 5,342,625 claim an improved formulation of cyclosporin in the form of a microemulsion pre-concentrate. In addition to the cyclosporin, this formulation requires a hydrophilic phase, a lipophilic phase, and a surfactant. The microemulsion pre-concentrate is claimed to provide enhanced bioavailability. As cyclosporin has a narrow therapeutic index and a short half-life, to provide adequate 24 hour protection it must be administered twice daily.

Cyclosporin A, available in soft gelatin capsule or oral suspension form, is indicated for the prevention of organ rejection in kidney, liver and heart transplants, for the treatment of severe active rheumatoid arthritis (RA) and severe recalcitrant plaque psoriasis. Other potential indications include Bechet's disease, anemia, nephrotic syndrome and Graft Versus Host Disease (GVHD), including Gastro-Intestinal Graft Versus Host Disease (GI-GVHD). Furthermore, a range or other diseases may benefit from treatment with cyclosporin A (Landford et al. (1998) Ann Intern Med; 128: 1021-1028).

Based on the poor and intra-subject bioavailability variability and the need for twice-daily administration, significant dose-related nephrotoxicity and hepatoxicity are side effect associated with long term use of cyclosporin A. When administered intravenously closporine A is known to be effective in the treatment of refractory ulcerative colitis (D'Haens et al., Gastroenterology 2001; 120:1323-1329). In a study by Sandborn et al. (J Clin Pharmacol, 1991; 31:76-80) the relative systemic absorption of cyclosporin following oral and intravenous as well as oil- and a water-based enemas was determined. Based on negligible plasma cyclosporin concentrations following enema administration, it was suggested that cyclosporin, even when solubilised, is poorly absorbed from the colon. The enemas however demonstrated considerable efficacy in the treatment of inflammatory bowel disease (Ranzi T, et al, Lancet 1989; 2:97). Orally administered cyclosporin demonstrated very limited efficacy in the treatment of inflammatory bowel disease.

Statements of Invention

According to the invention there is provided an oral cyclosporin composition comprising minicapsules having a core containing a cyclosporin in a solubilised liquid form, the minicapsules have a release profile to release the pre-solubilised cyclosporin at least in the colon.

In one embodiment the minicapsules have a release profile to also release pre-solubilised cyclosporine in the Ileum.

The minicapsules may have a release profile to also release pre-solubilised cyclosporin in the small intestine.

In one embodiment the cyclosporin is cyclosporin A. The cyclosporin A may be present in the core in an amount of from 2.5 to 25% w/w, preferably in an amount of from 2.5 to 10% w/w.

In one embodiment when exposed to a use environment less than 20% of the cyclosporin A is released within 4 hours, preferably when exposed to a use environment less than 10% of the cyclosporin A is released within 4 hours.

In one embodiment when exposed to a use environment less than 50% of the cyclosporin A is released within 12 hours, preferably when exposed to a use environment less than 35% of the cyclosporin A is released within 12 hours.

When exposed to a use environment preferably less than or equal to 100% of the cyclosporin A is released within 24 hours.

In one embodiment when exposed to a use environment less than 10% of the cyclosporin A is released within 4 hours, less than 35% of the cyclosporin A is released within 12 hours, and substantially all of the remaining cyclosporin A is released between 12 and 24 hours.

In another embodiment when exposed to a use environment less than 20% of the cyclosporin A is released within 4 hours, less than 50% of the cyclosporin A is released within 12 hours, and substantially all of the remaining cyclosporin A is released between 12 and 24 hours.

In a further embodiment when exposed to a use environment less than 10% of the Cyclosporin A is released within 6 hours, less than 30% of the cyclosporin A is released within 12 hours, less than 70% of the cyclosporin A is released within 18 hours and up to 100% of the cyclosporin A is released at 24 hours.

The minicapsules preferably comprise a solid shell containing the solubilised cyclosporin A. Usually the minicapsules are modified to provide the release profile.

In one case a modified release coating is applied to the outer shell of the minicapsules. Preferably a polymeric material is used to achieve modified release.

The polymeric material may be methacrylate and/or ethylcellulose.

In one embodiment the coating includes a dissolution enhancing agent. Preferably the dissolution enhancing agent is degraded by bacteria normally present in the lower gastrointestinal tract. The dissolution enhancing agent may be selected from one or more of pectin, amylose and alginate or derivatives thereof. In one case the dissolution enhancing agent is present in an amount of from 0.5 to 2% w/w of ethylcellulose.

In one embodiment the core comprises cyclosporin A, a solubilisation agent, a co-emulsifier, a surfactant, a permeability enhancer and a carrier. In one case the solubilisation agent comprises ethanol. The solubilisation agent may comprise triglycerides. The co-emulsifying agent may comprise fatty acid ester complexes. The surfactant agent may comprise fatty acid ester complexes. The permeability enhancing agent may comprise fatty acid ester complexes. In one case the carrier comprises a hydrophobic liquid, such as an oil, for example olive oil.

In one embodiment an outer shell layer of the minicapsules is modified to achieve modified release. In one case the liquid core of the minicapsules is modified to achieve modified release. Polymeric materials may be used to achieve modified release.

The cyclosporin is preferably released along the gastrointestinal tract in a form that maximises pre-systemic mucosal absorption. The cyclosporin may be released along the gastrointestinal tract in a form that maximises local gastrointestinal activity. The cyclosporin may be released along the gastrointestinal tract in a form that maximises gastrointestinal lumen activity. The cyclosporin may be released along the gastrointestinal tract in a form that maximises chronotherapy.

In one embodiment wherein the formulation contains an adhesive entity such as a muco- or bio-adhesive.

In one embodiment the composition comprises a hard gelatine capsule, a sprinkle, or a tablet containing the minicapsules.

In one case the minicapsules further comprise excipients to maximise solubility of the cyclosporin. The composition may further comprise excipients to maximise permeability of the cyclosporin at least along the gastrointestinal lining or mucosal lining. The composition may also comprise excipients to enhance the therapeutic potential of the cyclosporin in the ileum and colon. The excipients may be selected from one or more of absorption limiters, absorption enhancers, surfactants, co-surfactants, co-solvents, essential oils such as omega 3 oils, natural plant extracts such as neem, ion-exchange resins, anti-oxidants, polyethers, stabilizers, preservatives, bacteria degradable conjugation linkers such as azo bonds, polysaccharides such as amylose, guar gum, pectin, chitosan, inulin and cyclodextrins.

Preferably the composition facilitates mucosal absorption over 24 hours.

The composition may be used in treating or preventing inflammatory bowel disease; in treating ulcerative colitis; in treating Crohn's disease; for the treatment or prevention of graft-versus-host disease such as gastro-intestinal graft-versus-host disease; and/or in treating or preventing irritable bowel syndrome.

The composition may be presented for administration in paediatric formats.

The invention also provides a composition of the invention combined with another active pharmaceutical in a single oral dosage form.

BRIEF DESCRIPTION OF THE DRAWINGS

The invention will be more clearly understood from the following description of some embodiments thereof, given by way of example only, with reference to the accompanying drawings, in which:—

DETAILED DESCRIPTION

Figure 1:
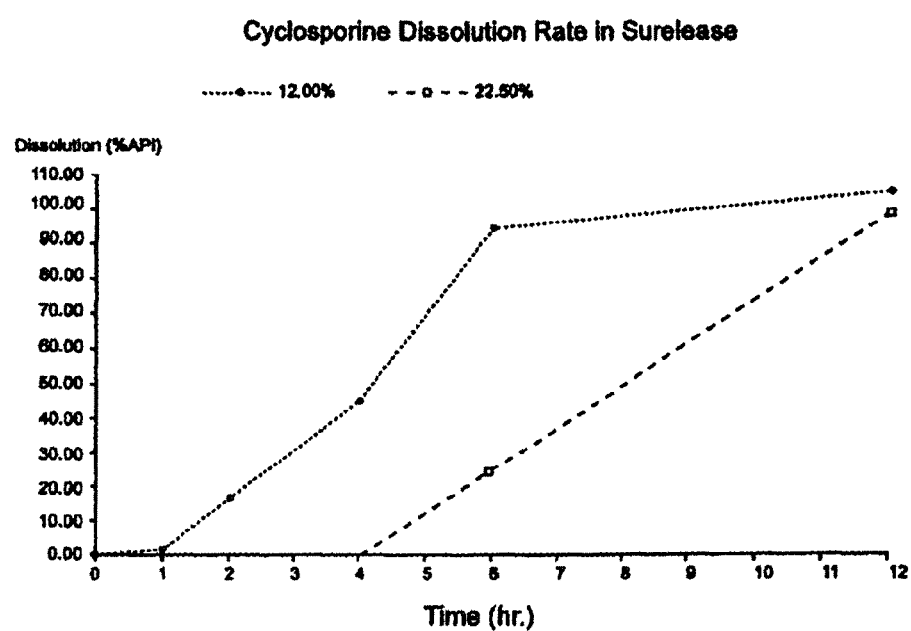
FIG. 1 is a graph showing the dissolution rate of Cyclosporin A from minicapsules coated with 12.8% and 22.5% weight gain Surlease™.

There is therefore a need for an improved pharmaceutical composition of cyclosporins. The invention enables the exploitation of the efficiency of cyclosporin in the treatment of ulcerative colitis. In the invention the cyclosporin remains in a soluble form in the colon and the systemic side effects associated with long-term high oral or intravenous doses of cyclosporin. A colon specific form that releases cyclosporin in a soluble form is provided.

The invention provides a method of preventing or treating an inflammatory or immune disorder, particularly relating to inflammatory or immune diseases that effect the gastrointestinal tract, in a subject while eliminating or reducing the toxicity associated with the administration of cyclosporin, through the orally delivered, colon-specific release of a therapeutically effective amount of cyclosporin in combination with a pharmaceutically acceptable carrier(s) or excipient(s).

The controlled release of active pharmaceutical agents is only truly useful if the agent is available to interact with its receptor or site of action in an active form. Unless the agent is in a fully soluble form it is unlikely to interact with its intended receptor or exert its desired action. The invention is a drug delivery format that enables the release cyclosporin from the format in soluble or readily-soluble form.

The invention provides an oral drug delivery technology that permits the colon-specific release of pre- or readily-solubilised cyclosporin in tandem with a controlled release formulation that permits release and absorption in the lining of the small intestine, the ileum and/or the colon to ensure a true once-daily formulation.

This once-daily technology which enables colon delivery of soluble cycloporine is advantageous as an effective drug delivery mechanism for enhanced treatment of diseases of colon, especially inflammatory- or ischemic-induced diseases, (ulcerative colitis, Crohn's disease, Gastro-Intestinal Graft Versus Host Disease (GI-GVHD) and other infections) whereby high local concentrations of soluble drug can be achieved while minimizing side effects that occur because of release of drugs in the upper GIT or unnecessary systemic absorption.

Cyclosporins are well known to have limited colonic absorption.

Additionally, for conditions that may affect the entire gastro-intestinal tract, including the small intestine, such as Crohn's Disease and GI-GVHD, a sustained release format of pre-solubilised cyclosporin, exhibiting limited systemic absorption is provided.

The invention enables the availability of cyclosporin in a soluble liquid. In addition to the active cyclosporin, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, fish, neem and sesame oils), polyethers (in particular substances like dimethyl isosorbide, dimethyl isoodide and dimethyl isomannide and mixtures of glyceryl monoesters of C8-C22 fatty acids and hexaglyceryl to pentadecaglyceryl monoesters of C8-C22 fatty acids in variable ratios from 1:3 to 1:8) glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and/or perfuming agents.

The invention enables successful colonic delivery. In the invention cyclosporin is protected from absorption in the environment of the upper gastrointestinal tract (GIT) but allows abrupt and/or sustained release into the proximal colon, which is the optimum site for colon-targeted delivery of cyclosporin. Such colon targeting is particularly of value for the treatment of diseases of colon such as Crohn's diseases, ulcerative colitis, and GVHD, including GI-GVHD.

The invention allows for a broad range of controlled release polymer coatings to be applied. Coating materials may include any combination of the commercially available acrylic-, methacrylic-, ethylcellulose-based polymers (such as, but not limited to the Eudragit™ and Surelease® range), as well as other polymers with natural polysaccharides, including, but not limited to amylose, pectin, alginate, amylopectin, chitosan, galactomannan, guar gum and any derivatives thereof, has the potential to customise how, where and when drugs are released from the underlying or embedded solid, semi-solid or liquid forms. In all examples cited in this specification, any specific polymer may be interchanged or combined with any other polymer to enable the required release profile according to the preferred optimal therapeutic outcome envisaged.

The invention provides a solid oral dosage form comprising the multiple minicapsule modified release composition of the present invention, the said minicapsules being one layer or multiple layer. Where a two layer minicapsule has a shell comprised of a gelling agent with a controlled release polymer or other coating or comprised of controlled release polymer or other materials.

In various embodiments comprising a membrane-controlled dosage form, the polymeric material comprises methacrylic acid co-polymers, ammonio methacrylate co-polymers, or mixtures thereof. Methacrylic acid co-polymers such as EUDRAGIT™ S and EUDRAGIT™ L (Evonik) are suitable for use in the controlled release formulations of the present invention. These polymers are gastroresistant and enterosoluble polymers. Their polymer films are insoluble in pure water and diluted acids. They dissolve at higher pHs, depending on their content of carboxylic acid. EUDRAGIT™ S and EUDRAGIT™ L can be used as single components in the polymer coating or in combination in any ratio. By using a combination of the polymers, the polymeric material can exhibit solubility at a pH between the pHs at which EUDRAGIT™ L and EUDRAGIT™ S are separately soluble.

The membrane coating can comprise a polymeric material comprising a major proportion (i.e., greater than 50% of the total polymeric content) of at least one pharmaceutically acceptable water-soluble polymers, and optionally a minor proportion (i.e., less than 50% of the total polymeric content) of at least one pharmaceutically acceptable water insoluble polymers. Alternatively, the membrane coating can comprise a polymeric material comprising a major proportion (i.e., greater than 50% of the total polymeric content) of at least one pharmaceutically acceptable water insoluble polymers, and optionally a minor proportion (i.e., less than 50% of the total polymeric content) of at least one pharmaceutically acceptable water-soluble polymer.

Ammonio methacrylate co-polymers such as EUDRAGIT™ RS and EUDRAGIT™ RL (Evonik) are suitable for use in the modified release formulations of the present invention. These polymers are insoluble in pure water, dilute acids, buffer solutions, or digestive fluids over the entire physiological pH range. The polymers swell in water and digestive fluids independently of pH. In the swollen state, they are then permeable to water and dissolved active agents. The permeability of the polymers depends on the ratio of ethylacrylate (EA), methyl methacrylate (MMA), and trimethylammonioethyl methacrylate chloride (TAMCl) groups in the polymer. Those polymers having EA:MMA:TAMCl ratios of 1:2:0.2 (EUDRAGIT™ RL) are more permeable than those with ratios of 1:2:0.1 (EUDRAGIT™ RS). Polymers of EUDRAGIT™ RL are insoluble polymers of high permeability. Polymers of EUDRAGIT™ RS are insoluble films of low permeability.

The amino methacrylate co-polymers can be combined in any desired ratio, and the ratio can be modified to modify the rate of drug release. For example, a ratio of EUDRAGIT™ RS: EUDRAGIT™ RL of 90:10 can be used. Alternatively, the ratio of EUDRAGIT™ RS: EUDRAGIT™ RL can be about 100:0 to about 80:20, or about 100:0 to about 90:10, or any ratio in between. In such formulations, the less permeable polymer EUDRAGIT™ RS would generally comprise the majority of the polymeric material with the more soluble RL, when it dissolves, permitting creating gaps through which solutes can enter the core and dissolved pharmaceutical actives escape in a controlled manner.

The amino methacrylate co-polymers can be combined with the methacrylic acid co-polymers within the polymeric material in order to achieve the desired delay in the release of the drug. Ratios of ammonio methacrylate co-polymer (e.g., EUDRAGIT™ RS) to methacrylic acid co-polymer in the range of about 99:1 to about 20:80 can be used. The two types of polymers can also be combined into the same polymeric material, or provided as separate coats that are applied to the core.

Eudragit™ FS 30 D is an anionic aqueous-based acrylic polymeric dispersion consisting of methacrylic acid, methyl acrylate, and methyl methacrylate and is pH sensitive. This polymer contains fewer carboxyl groups and thus dissolves at a higher pH (>6.5). The advantage of such a system is that it can be easily manufactured on a large scale in a reasonable processing time using conventional powder layering and fluidized bed coating techniques. In a study by Gupta et al (*Int J Pharm*, 213: 83-91, 2001) Eudragit FS 30 D demonstrated its potential for colonic delivery by resisting drug release up to pH 6.5 and the combination of Eudragit™ RL and RS proved successful for the sustained delivery of 5-ASA at the pH of the colon. Thus, Eudragit™ FS 30 D alone or with other controlled release polymers holds great potential to enable delivery of minicapsule formulations specifically to the colon.

In addition to the EUDRAGIT™ polymers described above, a number of other such copolymers can be used to control drug release. These include methacrylate ester co-polymers such as the EUDRAGIT™ NE and EUDRAGIT™ NM ranges. Further information on the EUDRAGIT™ polymers can be found in "Chemistry and Application Properties of Polymethacrylate Coating Systems," in Aqueous Polymeric Coatings for Pharmaceutical Dosage Forms, ed. James McGinity, Marcel Dekker Inc., New York, pg 109-114.

Several derivatives of hydroxypropyl methylcellulose (HPMC) also exhibit pH dependent solubility. Shin-Etsu Chemical Co., Ltd. esterified HPMC with phthalic anhydride to produce hydroxypropyl methylcellulose phthalate (HPMCP), which rapidly dissolves in the upper intestinal tract. Due to the limited compatibility of HPMCP with several types of plasticizers, hydroxypropyl methylcellulose acetate succinate (HPMCAS) was developed. The presence of ionizable carboxyl groups in the HPMCAS structure cause the polymer to solubilize at high pH (>5.5 for the LF grade and >6.8 for the HF grade). This polymer exhibits good compatibility with a variety of plasticizing agents and is commercially available from Shin-Etsu Chemical Co. Ltd. under the proprietary name AQOAT® in a powdered form to be redispersed in water.

Surelease® dispersion is a unique combination of film-forming polymer; plasticizer and stabilizers. Designed for sustained release and taste masking applications, Surelease is an easy-to-use, totally aqueous coating system using ethylcellulose as the release rate controlling polymer. The dispersion provides the flexibility to adjust drug release rates with reproducible profiles that are relatively insensitive to pH. The principal means of drug release is by diffusion through the Surelease dispersion membrane and is directly controlled by film thickness. Increasing or decreasing the quantity of Surelease® applied can easily modify the rate of release. With Surelease dispersion, reproducible drug release profiles are consistent right through from development to scale-up and production processes.

In addition to the EUDRAGIT™ and Surelease® polymers discussed above, other enteric, or pH-dependent, polymers can be used. Such polymers can include phthalate, butyrate, succinate, and/or mellitate groups. Such polymers include, but are not limited to, cellulose acetate phthalate, cellulose acetate succinate, cellulose hydrogen phthalate, cellulose acetate trimellitate, hydroxypropyl-methyl cellulose phthalate, hydroxypropylmethylcellulose acetate succinate, starch acetate phthalate, amylose acetate phthalate, polyvinyl acetate phthalate, and polyvinyl butyrate phthalate. Additionally, where compatible, any combination of polymer may be blended to provide additional controlled- or targeted-release profiles.

The coating membrane can further comprise at least one soluble excipient to increase the permeability of the polymeric material. Suitably, the at least one soluble excipient is selected from among a soluble polymer, a surfactant, an alkali metal salt, an organic acid, a sugar, and a sugar alcohol. Such soluble excipients include, but are not limited to, polyvinyl pyrrolidone, polyethylene glycol, sodium chloride, surfactants such as sodium lauryl sulfate and polysorbates, organic acids such as acetic acid, adipic acid, citric acid, fumaric acid, glutaric acid, malic acid, succinic acid, and tartaric acid, sugars such as dextrose, fructose, glucose, lactose, and sucrose, sugar alcohols such as lactitol, maltitol, mannitol, sorbitol, and xylitol, xanthan gum, dextrins, and maltodextrins. In some embodiments, polyvinyl pyrrolidone, mannitol, and/or polyethylene glycol can be used as soluble excipients. The at least one soluble excipient can be used in an amount ranging from about 1% to about 10% by weight, based on the total dry weight of the polymer. The coating process can be carried out by any suitable means, for example, by using a perforated pan system such as the GLATT, ACCELACOTA, Vector, Diosna, O'Hara, HICOATER or other such coating process equipment The modifications in the rates of release, such as to create a delay or extension in release, can be achieved in any number of ways. Mechanisms can be dependent or independent of local pH in the intestine, and can also rely on local enzymatic activity to achieve the desired effect. Examples of modified-release formulations are known in the art and are described, for example, in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,566.

With membrane-modified extended-release dosage forms, a semi-permeable membrane can surround the formulation containing the active substance of interest. Semi-permeable membranes include those that are permeable to a greater or lesser extent to both water and solute. This membrane can include water-insoluble and/or water-soluble polymers, and can exhibit pH-dependent and/or pH-independent solubility characteristics. Polymers of these types are described in detail below. Generally, the characteristics of the polymeric membrane, which may be determined by, e.g., the composition of the membrane, will determine the nature of release from the dosage form.

In particular, the present invention provides for formulations of minicapsules or minispheres wherein the modified release is dependent upon, where appropriate, any one of the core formulation constituents, the shell composition or the shell coating. The minicapsules or minispheres may be produced through the utilisation of surface tension of one or more different solutions which when ejected through an orifice or nozzle with a certain diameter and subject to specific frequencies and gravitational flow, forms into a spherical form and falls into a cooling air flow or into a cooling or hardening solution and the outer shell solution where it is gelled or solidified. This briefly describes the formation of seamless minispheres. According to prior art the core solution is mainly a hydrophobic solution or suspension. The outer shell solution can be any gel forming agent but is normally gelatine- or alginate-based based but may also include polymers or other materials that enable controlled release. With the nozzle having two orifices (centre and outer), a hydrophobic solution can be encapsulated. Where appropriate, it may be possible that both the core and/or shell may be comprised of a material or material composites that have been processed by a wet- or dry-extrusion mechanism, melt or otherwise fluidized prior to mixing or extrusion. Ideally, to enable drug content and release consistency, it is preferred that all processes will result in fairly uniform morphologies with a relatively smooth surface to facilitate quite even coating layers to be added in a uniform manner. With the nozzle having one or more orifices seamless minicapsules for various applications can be processed using minicapsule processing equipment enabled by, but not limited to, Freund Spherex, ITAS/Lambo Globex or Inotech processing equipment. As outlined above the coating process can be carried out by any suitable means, for example, by using a perforated pan or fluidized-based system such as the GLATT, Vector, ACCELACOTA, Diosna, O'Hara and/or HICOATER processing equipment. Seamless minicapsules may be manufactured using the method described in U.S. Pat. No. 5,882,680 (Freund), the entire contents of which we incorporated herein by reference.

The invention relates to drug delivery in the colon which has been largely overlooked from a drug delivery perspective. Mainly having evolved to regulate electrolyte balance and to further breakdown complex carbohydrate structures there is a significant flow of water from the colonic lumen into the body. In addition, the colon is home to a natural bacterial flora to degrade complex carbohydrates to ensure effective excretion, provide much needed fibre and some nutrient absorption. With a much lower concentration of proteolytic and other enzymes populated in the colon, it is a much more benign environment for proteins and peptides as well as other biological entities such as carbohydrates and nucleic acids. From a drug delivery perspective, the colon presents a number of interesting possibilities: the bacteria can be harnessed to break down controlled release coatings that are resistant to acidic breakdown as well as pH differentials; the benign environment ensure than active pharmaceuticals, including biopharmaceuticals, are less likely to be degraded if released locally into the colon; the almost continuous flow of fluids from the colonic lumen to the bloodstream may be harnessed to carry hydrophilic entities from the intestine to the lumen. Finally, the long transit time in the colon, ranging form 10-20 hours provides greater residence and potential for interaction with the colonic mucus and epithelial cells leading to enhanced absorption into the cells lining the colonic lumen and beyond.

A barrier to effective colonic delivery of hydrophobic and lipophilic drugs is that the colon did not evolve to solubilize foodstuffs and other entities but rather to ensure electrolyte balance and maximise fibre breakdown and fermentation. The colon remains very porous to hydrophilic entities. By delivering hydrophobic or lipophilic drugs to the colon in a pre-solubilised or readily soluble format and releasing such in the colon, the potential for absorption, local or systemic, is enhanced significantly. The present invention permits the encapsulation of pre-solubilized or readily soluble drugs in liquid or hydrolysable semi-solids or solids into the minicapsule core and then modulation of the shell to include intestinal- or colon-controlled release polymers or coating the shell with same. The result is release of optimized formulations at specific sites along the intestinal tract for maximal therapeutic efficacy or systemic absorption.

Likewise, delivery of formulations that are readily broken down in an aqueous environment or a bacteria rich environment has the potential, when coated with colon-specific controlled release polymers or include entities that are degraded by bacteria have the potential to protect susceptible entities from the gastric or intestinal environment yet ensure that they are released intact in the colon where, once liberated, will be readily absorbed. Redox-sensitive, pectin, alginate, chitosan or other bacterially susceptible polymer-based matrices, coatings or other sustained release formulations, liquid, semi-solid or solid, can be encapsulated into or coated onto one- or multi-layered minicapsules.

The formulations of the present invention can exist as a multi-unit or as multi-unit minicapsules in a single-unit format. The term "multi-unit" as used herein means a plurality of discrete or aggregated minicapsules. Single-unit formulations include, for example, tablets, hard gelatin capsules, caplets, and pills.

The methods and formulations of the present invention are intended to encompass all possible combinations of components that exhibit modified-release and immediate-release properties. For example, a formulation and/or method of the invention can contain components that exhibit extended-release and immediate-release properties, or both delayed-release and immediate-release properties, or both extended-release and delayed-release properties, or a combination of all three properties. For example, a multi-minicapsule or multi-minisphere formulation including both immediate-release and extended-release components can be combined in a capsule, which is then coated with an enteric coat to provide a delayed-release effect. Or, for example, a delayed- and extended-release caplet may comprise a plurality of discrete extended-release particles held together with a binder in the caplet, which is coated with an enteric coating to create a delay in dissolution.

As used herein, the term "modified-release" formulation or dosage form includes pharmaceutical preparations that achieve a desired release of the drug from the formulation. A modified-release formulation can be designed to modify the manner in which the active ingredient is exposed to the desired target. For example, a modified-release formulation can be designed to focus the delivery of the active agent entirely in the distal large intestine, beginning at the cecum, and continuing through the ascending, transverse, and descending colon, and ending in the sigmoid colon. Alternatively, for example, a modified-release composition can be designed to focus the delivery of the drug in the proximal small intestine, beginning at the duodenum and ending at the ileum. In still other examples, the modified-release formulations can be designed to begin releasing active agent in the jejunum and end their release in the transverse colon. The possibilities and combinations are numerous, and are clearly not limited to these examples.

The term "modified-release" encompasses "extended-release" and "delayed-release" formulations, as well as formulations having both extended-release and delayed-release characteristics. An "extended-release" formulation can extend the period over which drug is released or targeted to the desired site. A "delayed-release" formulation can be designed to delay the release of the pharmaceutically active compound for a specified period. Such formulations are referred to herein as "delayed-release" or "delayed-onset" formulations or dosage forms. Modified-release formulations of the present invention include those that exhibit both a delayed- and extended-release, for example, formulations that only begin releasing after a fixed period of time or after a physicochemical change has occurred, for example, then continue releasing over an extended period.

As used herein, the term "immediate-release formulation," is meant to describe those formulations in which more than about 50% of active ingredient is released from the dosage form in less than about 2 hours. Such formulations are also referred to herein as "conventional formulations."

As used herein, the phrase "drug-release profile that is independent of surrounding pH" means effectively a drug composition comprising a polymeric system that is non-enteric or whose permeability and solubility properties do not change with environmental, i.e., external, pH. Meaning, a drug composition having release characteristics such as dissolution is substantially unaffected by pH or regardless of pH-changes in the environment. This is in comparison to a release profile that is pH-dependent where the release characteristics vary according to the pH of the environment.

Intestinal Diseases

Gastrointestinal conditions pose a significant worldwide health problem. Inflammatory bowel diseases, which genus encompass a range of diseases including Crohn's disease and ulcerative colitis, affect nearly 1 million people in the United States each year. The two most common inflammatory conditions of the intestine, ulcerative colitis (UC) and Crohn's disease (CD) are collectively known as inflammatory bowel disease (IBD). These conditions are diseases of the distal gut (lower small intestine, large intestine, and rectum) rather than the proximal gut (stomach and upper small intestine). Between the two, ulcerative colitis primarily affects the colon, whereas Crohn's disease affects the distal small intestine as well.

Inflammatory Bowel Disease (IBD)

Although they are distinct IBD conditions, the same drugs are commonly used to treat both UC and CD. Drugs commonly used in their treatment include steroids (e.g., budesonide and other corticosteroids, and adrenal steroids such as prednisone and hydrocortisone); cytokines such as interleukin-10; antibiotics; immunomodulating agents such as azathioprine, 6-mercaptopurine, methotrexate, cyclosporin, and anti-tumor necrosis factor (TNF) agents such as soluble TNF receptor and antibodies raised to TNF; and also antiinflammatory agents such as zinc. The most commonly prescribed agents for IBD include sulfasalazine (salicyl-azo-sulfapyridine, or "SASP") and related 5-aminosalicylic acid ("5-ASA") products, including mesalazine. In refractory cases of the disease, high doses of cyclosporin, administered intravenously, has demonstrated considerable and rapid efficacy.

Inflammation of the ileum (the farthest segment of the small intestine) due to Crohn's disease is known as iletis. When both the small intestine and the large intestine are involved, the condition is called Crohn's enterocolitis (or ileocolitis). Other descriptive terms may be used as well. Diagnosis is commonly made by x-ray or colonoscopy. Treatment includes medications that are anti-inflammatories, immune suppressors, or antibiotics. Surgery can be necessary in severe cases. Crohn's disease is an area of active research around the world and new treatment approaches are being investigated which have promise to improve the lives of affected patients.

Gastrointestinal Graft-Versus-Host-Disease (GI-GVHD)

GI GVHD is a life-threatening condition and one of the most common causes for bone marrow and stem cell transplant failure. These procedures are being increasingly used to treat patients with leukemia and other cancers to eliminate residual disease and reduce the likelihood of relapse. Unlike solid organ transplants where the patient's body may reject the organ, in GVHD it is the donor cells that begin to attack the patient's body—most frequently the gut, liver and skin. Patients with mild-to-moderate GI GVHD typically develop symptoms of anorexia, nausea, vomiting and diarrhea. If left untreated, GI GVHD can progress to ulcerations in the lining of the GI tract, and in its most severe form, can be fatal. Systemic immunosuppressive agents such as prednisone, which are the current standard treatments for GI GVHD, are associated with high mortality rates due to infection and debility. Further, these drugs have not been approved for treating GI GVHD in the U.S. or European Union, but rather are used off-label as investigational therapies for this indication.

The current invention permits the release of cyclosporin A to the colon in a novel oral, locally acting active therapy which will reduce the need for systemic immunosuppressive drugs such as prednisone, which is currently used to prevent and control GI GVHD. Drugs such as prednisone have the unwanted and potentially dangerous side effects of weakening the patient's immune system leaving them susceptible to opportunistic infections as well as substantially inhibiting the intended anti-cancer effect of bone marrow and stem cell transplants. The current colon-targeted immunosuppressant invention is designed to reduce the need for systemic immunosuppressive drugs and thereby improve the outcome of bone marrow and stem cell transplantation.

Cyclosporin is recognized, on- and off-label, as common treatments for IBD and is widely used for this purpose. However, high dose cyclosporin exhibits significant problems, including side effects to be detailed hereinafter. Additionally, both exhibit a half-life and efficacy profile that is less than maximal, reflected in high and multiple daily doses, lower response and remission rates, and higher relapse rates, related to its site and mechanism of action and efficiency of delivery to the cells of the distal gut. Extensive Cyclosporin absorption from the small intestine reduces its availability at distal sites in the gut, which are the sites of the therapeutic effect and the preferred sites of delivery, thereby necessitating high doses to be administered. Ideally, the cyclosporin should reach the distal gut (ileum and/or colon) in unchanged form, but not be absorbed into the systemic circulation as the parent compound from there. The absorption into the systemic circulation from proximal and/or distal sites as the parent compound results in side effects associated with the absorbed drug and its systemic effects. Existing oral dosage forms of cyclosporin, namely soft gelatine capsule or oral suspension, are unsuited to controlled or ileum/colon targeted release. Additionally, rectally administered suppositories or enemas are inconvenient and painful.

To overcome systemic side effects and the need to administer high doses frequently, the current invention proposes first formulating either cyclosporin as a solubilised formulation, encapsulating with a gelling agent to produce minicapsules. The encapsulating agent may contain controlled release polymers that release only in the ileum or colon or may be coated with a polymer or other coating that results in same. The advantages are several-fold, including: reduced systemic absorption of the active cyclosporin or tacrolimus which is known to result in dose related toxicities, including nephrotoxicity, release of sufficient dose of cyclosporin in soluble form as well as a broad distribution of cyclosporin throughout the colon. Furthermore, incorporating a mucoadhesive into the encapsulating shell or coating the encapsulating shell with a mucoadhesive may ensure that the minicapsules are in contact with the colonic mucus layer prior to releasing the active proximal to the diseased tissue. For certain Crohn's Disease sub-groups it may be required to enable release throughout the gastrointestinal tract, including the small intestine. Likewise for GI-GVHD, it may be beneficial to have sustained release throughout the entire gastrointestinal tract from small intestine to colon.

Certain natural extracts, including Neem oil, aloe vera, tripala, tumeric and other essential oils, including the omega polyunsaturated oils such as EPA, DHA, conjugated linoeic acid (CLA) and other derivatives thereof, have potential as treatments to alleviate or prevent inflammatory bowel disease as well as other intestinal disorders, including gastric, duodenal and intestinal ulcers. Additionally, certain plant extracts, including berry extracts such as blueberry, achi, resorcinolic/phenolic lipids, resveratrol, flavanoids and derivatives thereof, alone or in combination, have potential application in IBD and IBS and other intestinal or systems conditions. The mode of action of berry extracts, such as blueberry extract, remains uncertain but has effect on intestinal motility, stool formation and colonic flora. Yet other potential therapeutics include, but are not limited to, proteins, therapeutic peptides, vaccines, antibodies or fragments thereof. Local delivery to the mucosa will overcome degradation and ensure that a high local concentration is available to enhance therapeutic efficacy. Encapsulating any of the above, alone or in any combination, into minicapsules or minispheres and targeting the release to areas of the intestine that are diseased provide for enhanced disease management as well as perhaps a reduction in any potential for systemic side effects. Furthermore, certain oils, including the essential oils, DHA and EPA are known to increase the absorption of certain entities throughout the gastrointestinal tract, including the colon.

This invention is advantageous in providing methods and formulations for treating or preventing inflammatory bowel disease. The invention proposes delivering effective concentrations of pre-solubised Cyclosporin, Tacrolimus, Sirolimus, Hydralazine, DMOG, others or derivatives thereof, to affected areas of the gastrointestinal tract, with minimized systemic absorption of parent drug. The invention is directed to, among other things, a pharmaceutical composition for administration to a subject in need thereof comprising a dose of an active pharmaceutical compound, and pharmaceutically acceptable salts, esters and pro-drugs thereof, and at least one pharmaceutically acceptable excipient, wherein the composition exhibits localized release and exhibits:

For Ulcerative Colitis and Crohn's Disease—a dissolution profile, when tested in a U.S.P. Type II apparatus (paddles) at 37.degree.C. and 50 rpm, in pH 6.8 buffer for the test: Up to 4 hours: less than or equal to about 20% drug released; 6 hours: less than or equal to about 35% drug released; 8 hours: less than or equal to about 50% drug released; 12 hours: less than or equal to about 60% drug released; 18 hours: less than or equal to about 75% drug released; and 24 hours: from about 25% to about 100% drug released.

For GI-GVHD—a dissolution profile, when tested in a U.S.P. Type II apparatus (paddles) at 37.degree.C. and 50 rpm, in pH 6.8 buffer for the test: 1 hour: less than or equal to about 20% drug released; 4 hours: less than or equal to about 35% drug released; 6 hours: less than or equal to about 50% drug released; 12 hours: less than or equal to about 60% drug released; 16 hours: less than or equal to about 75% drug released; and 24 hours: from about 25% to about 100% drug released.

This invention relates to formulations and methods for treating or preventing inflammatory bowel disease. The term "inflammatory bowel disease" includes, but is not limited to, ulcerative colitis, Crohn's disease and GI-GVHD. Other treatable conditions would include but are not limited to ischemic bowel diseases; necrotizing enterocolitis, intestinal lesions associated with thermal burns and leukotriene $B_4$-mediated diseases; intestinal inflammations/allergies such as Coeliac diseases, proctitis, eosinophilic gastroenteritis, mastocytosis; food-related allergic diseases which have symptomatic manifestation remote from the gastro-intestinal tract (e.g., migraine, rhinitis and eczema).

This invention relates to formulations and methods for treating or preventing inflammatory bowel disease. The term "inflammatory bowel disease" includes, but is not limited to, ulcerative colitis, Crohn's disease and GI-GVHD. Other treatable conditions would include but are not limited to ischemic bowel diseases; inflammatory bowel diseases, necrotizing enterocolitis, intestinal lesions associated with thermal burns and leukotriene $B_4$-mediated diseases; intestinal inflammations/allergies such as Coeliac diseases, proctitis, eosinophilic gastroenteritis, mastocytosis, Crohn's disease and ulcerative colitis; food-related allergic diseases which have symptomatic manifestation remote from the gastro-intestinal tract (e.g., migraine, rhinitis and eczema).

As cyclosporin blocks T-cell activation, a prerequisite for HIV proliferation, it may be useful as a prophylactic for the prevention of HIV replication. In the particular cases of HIV-1, HIV-2 and related retroviral strains, inhibition of T-cell mitosis would suppress the replication of the virus, since the virus relies upon the host T-cell's proliferative functions to replicate. The formulations in the invention would be useful when used alone, or in combination therapy with other immunosuppressants, for example, but not limited to, FK506, rapamycin, picibanil, mycophenolic acid, azathioprine, prednisolone, cyclophosphamide, brequinar, sequinivir and leflunomide as a prophylactic for the prevention of HIV replication which is rapid in the gastrointestinal tract following infection. In the particular cases of HIV-1, HIV-2 and related retroviral strains, inhibition of T-cell mitosis would suppress the replication of the virus, since the virus relies upon the host T-cell's proliferative functions to replicate.

The present invention provides a multiple minicapsule modified release composition comprising at least one population of cyclosporin-containing minicapsules which, upon administration to a patient, exhibits a single, bimodal or multimodal release profile throughout the entire gastrointestinal tract or at pre-specified regions along the gastrointestinal tract.

The multiple minicapsule modified release composition may comprise at least two populations of cyclosporin-containing minicapsules which, upon administration to a patient, exhibits a bimodal or multimodal release profile that results in a plasma profile within therapeutically effective pharmacokinetic parameters, as appropriate.

In one case the invention provides a multiple minicapsule modified release composition comprising at least two populations of active ingredient-containing minicapsules which, upon administration to a patient, exhibits a pulsatile release profile.

The invention provides a multiple minicapsule modified release composition to protect or degradative-enzyme sensitive active ingredients and to release such proximal to the intestinal epithelial cell wall or in the colon, in the lumen or proximal to the epithelial wall in the small intestine or colon.

In one case the invention provides a multiple minicapsule modified release composition whereby the active or actives are released in the ileum or colon, where the active is not absorbed but may yet be locally active.

The pharmaceutically acceptable excipient may be chosen from carriers, fillers, extenders, binders, humectants, disintegrating agents, solution-retarding agents, absorption accelerators, wetting agents, absorbents, lubricants, stabilizers, surfactants, solubilising agents, permeability enhancers, oils, plant extracts, fish extracts, marine extracts, colouring agents, buffering agents, dispersing agents, preservatives, organic acids, and organic bases.

The invention also provides a sachet format comprising multiple minicapsule modified release composition of the present invention for ease of administration to paediatrics, geriatrics or other patient populations with swallowing difficulties, including patients who are fed by tube.

The invention will be more clearly understood from the following examples.

EXAMPLES

Figure 11:
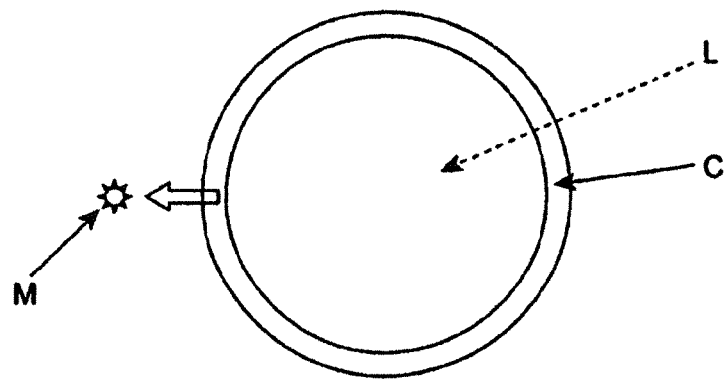
FIG. 11 is a schematic illustration of the minicapsule form used in the formalities of the invention.

FIG. 11 schematically illustrates—liquid-filled minicapsules with controlled release polymer coatings. This format comprises solubilised cyclosporin encapsulated in a core C encapsulated using a suitable gelling agent that is further coated to permit controlled or targeted release along the gastrointestinal tract. The cyclosporin is in an enhanced solubilised form, as a liquid L. The open arrow represents the release of the drug molecule M into the gastrointestinal, where it is fully soluble when released.

Example 1

Ileum- and Colon-Specific Cyclosporin A

The core formulation was prepared as follows. Cylosporine A was dissolved in a suitable volume of ethanol. Once dissolved, the solution was blended with a suitable mix of Labrafil and Olive oil. The shell solution was prepared as follows: Appropriate quantities of gelatin and sorbitol were added to water and heated to 70 degrees C. until in solution. The minicapsules were prepared using a Spherex Labo to produce 2-layer minicapsules, the core of which comprises Cylosporine A in an enhanced solubilised and permeabilised formulation. In addition, the core formulation does enable a degree of sustained release.

TABLE 1

Ileum- and Colon-specific Cyclosporin A

| Ingredients | % w/w |
|---|---|
| Core Composition | |
| Cyclosporin A | 16.70 |
| Labrafil M 1944 CS | 18.2 |
| Olive Oil | 65 |
| Ethanol | 0.1 |
| Shell Composition | |
| Gelatin | 90.0 |
| Sorbitol | 10.0 |

To enable an ileum- and colon-specific product, the minicapsules can be coated either with a sustained release polymer or a combination of colonic-specific polymer and sustained release polymers. The following options have been developed and tested:

Example 2

FIG. 1 illustrates Cyclosporin A release from the minicapsules of Example 1 coated with 12.% and 22.5% weight gain Surelease®.

Example 3

Figure 5:
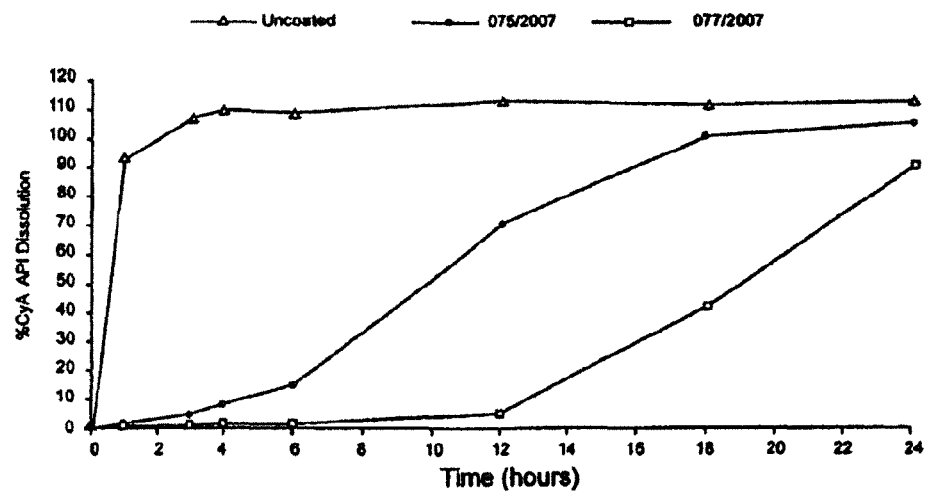
FIG. 5 is a graph showing the dissolution rate of Cyclosporin A from uncoated minicapsules (uncoated), minicapsules coated with 22% weight gain Eudragit™ RS (076/2007) and minicapsules coated with 22% weight gain Eudragit™ RS plus 14% weight gain Eudragit™ FS30D (077/2007) in 0.75% SDS (99)

Eudragit™ RS—Cyclosporin A containing minicapsules of example 1 were coated with Eudragit™ RS with or without further coating with Eudragit™ FS30D. The resulting dissolution profiles demonstrate the possibility to delay the release of the active for a number of hours and thereafter to release it in a sustained manner. The results are displayed in FIG. 5.

Example 4

Figure 6:
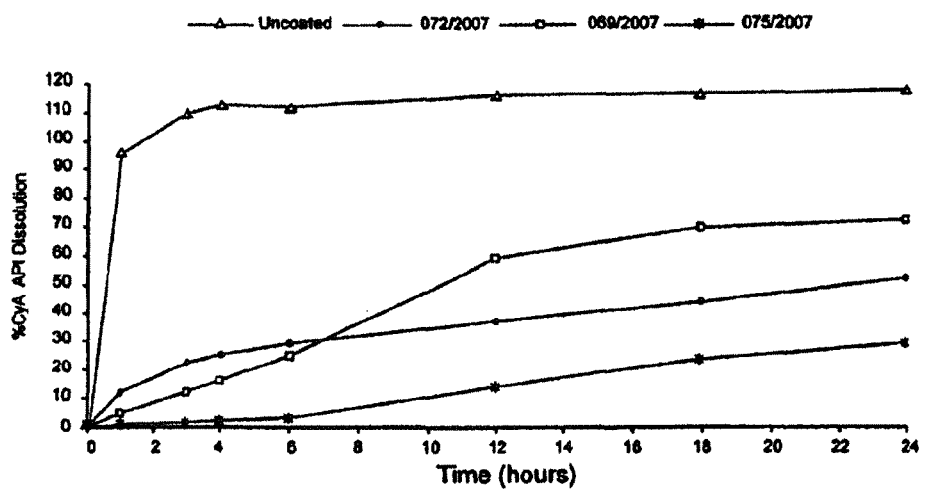
FIG. 6 is a graph showing the dissolution rate of Cyclosporin A from uncoated minicapsules (uncoated) and with minicapsules coated with 22% (069/2007) and 37% (072/2007) weight gain Surlease® as well as 22% weight gain Surelease® plus 14% weight gain Eudragit™ FS30D (075/2007) in 0.75% SDS (99)

Surelease®—Cyclosporin A containing minicapsules of Example 1 were coated with Surelease® with or without further coating with Eudragit™ FS30D. The resulting dissolution profiles demonstrate the possibility to delay the release of the active for a number of hours and thereafter to release it in a sustained manner. The results are displayed in FIG. 6.

Example 5

Figure 7:
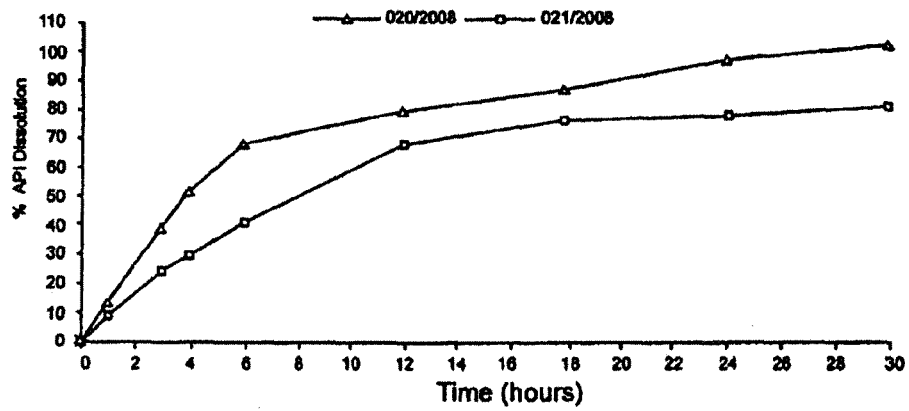
FIG. 7 is a graph showing the dissolution rate of Cyclosporin A from minicapsules coated with 20% weight gain Surlease®/1% Pectin (020/2008) and 20% weight gain Surlease®/1% Pectin plus 9% weight gain Eudragit FS30D (021/2008) in 0.75% SDS (99)
Figure 8:
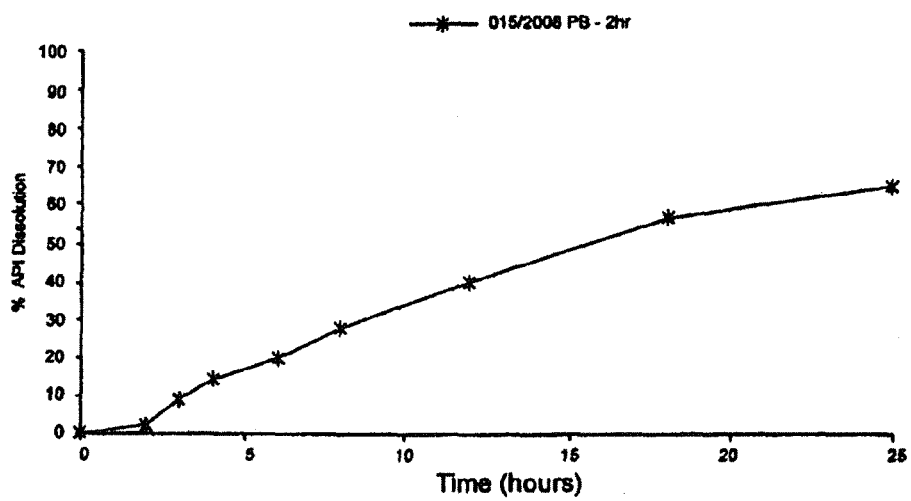
FIG. 8 is a graph showing the dissolution rate of Cyclosporin A from minicapsules coated with 20% weight gain Surlease®/1% Pectin plus 11% weight gain Eudragit FS30D following 2 hours in pH 7.4% phosphate buffer solution followed by 22 hours in 0.75% SDS dissolution media.

Surelease® and Pectin—Cyclosporin A containing minicapsules of example 1 were coated with Surelease®, with or without the inclusion of high or low molecular weight pectin in the coating solution and with or without further coating the mincapsules with the pH sensitive Eudragit™ FS30D. The resulting dissolution profile demonstrates the possibility to delay the release of the active for a number of hours and thereafter to release it in a sustained manner. The results are displayed in FIG. 7 and FIG. 8.

Example 6

Figure 9:
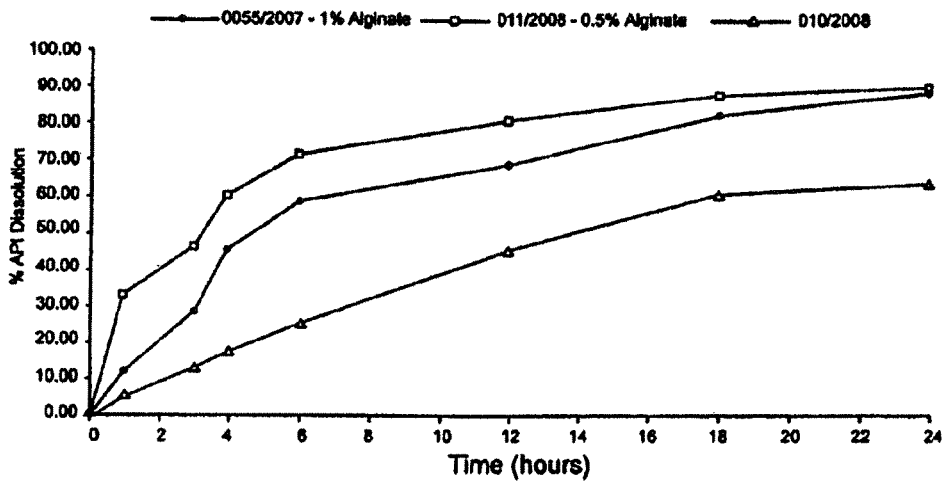
FIG. 9 is a graph showing the dissolution rate of Cyclosporin A from minicapsules coated with 13% weight gain Surlease® (013/2008) 13 weight gain Surelase®/1% Sodium Alginate (005/2008) and 13% weight gain Surlease®/0.5% Sodium Alginate (011/2008) in 0.75% SDS.
Figure 10:
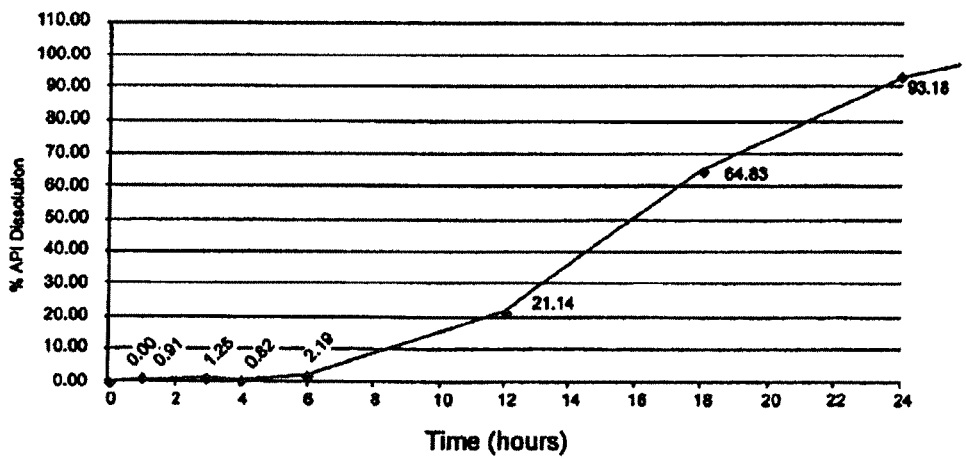
FIG. 10 is a graph showing the dissolution rate of cyclosporin A from minicapsules coated with 22% Eudragit™ RS30D.

Surelease® and Alginate—Cyclosporin A containing minicapsules of example 1 were coated with Surelease®, with or without the inclusion of alginate in the coating solution and with or without further coating the mincapsules with the pH sensitive Eudragit™ FS30D. The resulting dissolution profile demonstrates the possibility to delay the release of the active for a number of hours and thereafter to release it in a sustained manner. The results are displayed in FIG. 9.

Example 7

A once-daily formulation comprises minicapsules of example 1 containing cyclosporine A coated with 22% weight gain Eudragit™ RS30D to provide less than 10% release up to 6 hours, less than 30% up to 12 hours, less than 70% up to 18 hours and up to 100% at 24 hours. The results are displayed in FIG. 11.

Example 8

Ileum- and Colon-Specific Cyclosporin A

The core formulation was prepared as follows. Cylosporine A was dissolved in a suitable volume of ethanol. Once dissolved, the solution was blended with a suitable mix of Labrafil and Olive oil. The shell solution was prepared as follows: Appropriate quantities of gelatin and sorbitol were added to water and heated to 70 degrees C. until in solution. The minicapsules were prepared using a Spherex Labo to produce 2-layer minicapsules, the core of which comprises Cylosporine A in an enhanced solubilised and permeabilised formulation. In addition, the core formulation does enable a degree of sustained release.

TABLE 2

Ileum- and Colon-specific Cyclosporin A

| Ingredients | % w/w |
|---|---|
| Core Composition | |
| Cyclosporin A | 2.5-25 |
| Labrafil M 1944 CS | 15-35 |
| Essential Oil | 0-80 |
| Olive Oil | 0-80 |
| Ethanol | 0-20 |
| Shell Composition | |
| Gelatin | 90.0 |
| Sorbitol | 10.0 |

To enable an ileum- and colon-specific product, the minicapsules can be coated either with a sustained release polymer or a combination of colonic-specific polymer and sustained release polymers.

Example 9

Ileum- and Colon-Specific Cyclosporin and Neem

The core formulation was prepared as follows. Cylosporine A was dissolved in a suitable volume of ethanol. Once dissolved, the solution was blended with a suitable mix comprising one or more of Labrafil, Olive oil, Neem oil or other essential oils, including omega-3-rich fish oils. The shell solution was prepared as follows: Appropriate quantities of gelatin and sorbitol were added to water and heated to 70 degrees C. until in solution. The minicapsules were prepared using a Spherex Labo to produce 2-layer minicapsules, the core of which comprises Cylosporine A in an enhanced solubilised and permeabilised formulation. In addition, the core formulation does enable a degree of sustained release.

TABLE 3

Ileum- and Colon-specific Cyclosporin and Neem

| Ingredients | % w/w |
|---|---|
| Core Composition | |
| Cyclosporine | 0-20 |
| Labrafil | 0-35 |
| Neem | 0-75 |
| Olive Oil | 0-75 |
| Essential Oil | 0-75 |
| Ethanol | 0-20 |
| Shell Composition | |
| Gelatin | 90.0 |
| Sorbitol | 10.0 |

To enable an ileum- and colon-specific product, the minicapsules are coated either with a sustained release polymer or a combination of colonic-specific polymer and sustained release polymers. The sustained release coating comprises a 95:5 ratio of Eudragit™ RS: Eudragit™ RL. The combination comprises 95:5 Eudragit™ RS:RL, further coated with Eudragit FS30D.

Example 10

Colon-Specific, Pre-Solubilized Cyclosporin for Treatment of IBD

Figure 2:
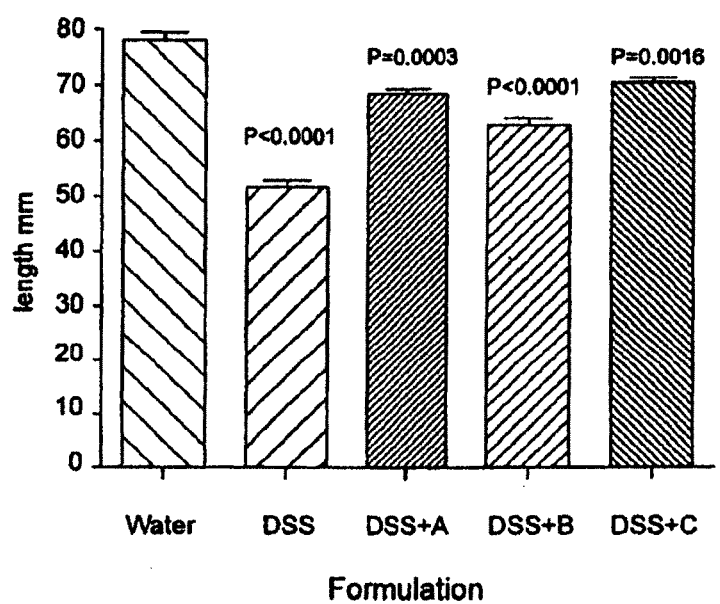
FIG. 2 is a bar chart showing the colon length of DSS-induced colitis mice treated with Capsule A (0.25 mg CyA/day; immediate release), Capsule B (0.25 mg CyA/day; ileum release) and Capsule C (0.25 mg CyA/day; colon release) for 7 days, with 6 mice in each group.

Colitis was induced in mice using DSS 2.5% in drinking water. To determine the effectiveness of pre-solubilized cyclosporin on the prevention or treatment of DSS-induced colitis various formulations of pre-solubilized cyclosporin minicapsules with differing release profiles were administered to mice daily. The minicapsules were prepared using the method described in Example 1 above. Referring to FIG. 2, in total, three Cyclosporin (0.25 mg/mouse/day) mini-formulations were used in the study, namely A (Immediate Release—small intestine: Uncoated minicapsules containing cyclosporin A as per Example 1), B (Ileum Release—sustained release: Minicapsules containing cyclosporin A as per Example 1, coated with a 12.5% weight gain Eudragit™ RS30D polymer coating) and C (Colon-specific Release—sustained release: Minicapsules containing cyclosporin A as per Example 1, coated with a 22% weight gain Eudragit™ RS30D polymer coating).

Following removal of the colon from mice on Day 7, it is observed that while the DSS still exerted a shortening affect on the colon length, the administration of all CyA formats, particularly the colon-specific CyA resulted in significantly reduced colon shortening, thereby suggesting that CyA is exerting a protective effect against DSS-induced colitis.

Figure 3:
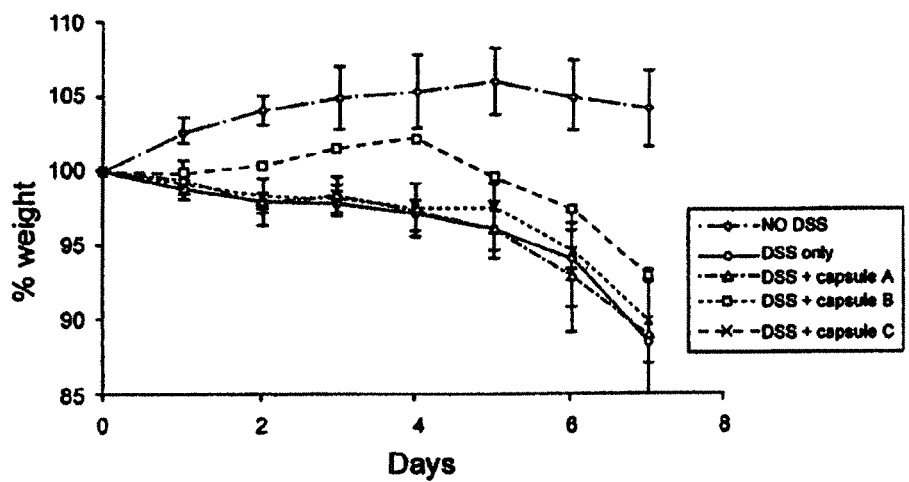
FIG. 3 is a graph showing the average weight of DSS-induced colitis mice treated with Capsule A (0.25 mg CyA/day; immediate release), Capsule B (0.25 mg CyA/day; ileum release) and Capsule C (0.25 mg CyA/day; colon release)

A major symptom of DSS-induced colitis is weight loss. From FIG. 3 it is evident that when administered directly to the colon, 0.25 mg CyA (Capsule C) administered daily has a significant protective effect compared mice administered with immediate (Capsule A) or ileum-release (Capsule B) CyA. This data set suggests that when administered specifically to the colon daily at low concentration; CyA has a pronounced protective effect on DSS-induced colitis.

Figure 4:
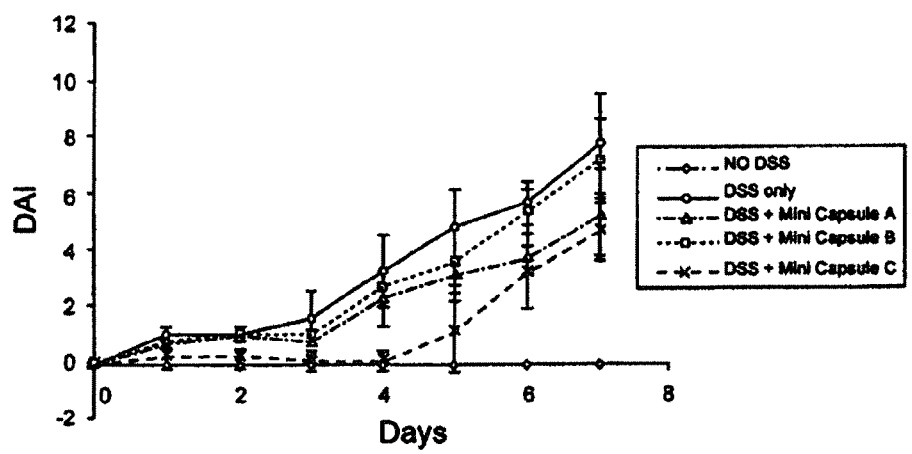
FIG. 4 is a graph showing the Disease Activity Index (DAI) of DSS-induced colitis mice treated with Capsule A (0.25 mg CyA/day; immediate release), Capsule B (0.25 mg CyA/day; ileum release) and Capsule C (0.25 mg CyA/day; colon release) for 7 days, with 6 mice in each group.

Referring to FIG. 4, the disease activity index (DAI) is calculated as the sum of scores of weight loss, stool consistency and blood in feces. Normal stool=formed pellets; loose stool=pasty and semi-formed stool which do not stick to the anus; diarrhoea=liquid stools that stick to the anus. This composite scoring system clearly demonstrates that daily administration of 0.25 mg CyA specifically to the colon (DSS-COAT beads) produces a pronounced protective effect against the induction of colitis in DSS treated mice.

Formulations and uses based on cyclosporin A are described above. However, it will be appreciated that the invention can also be applied to other cyclosporins including cyclosporins-B, -C, -D, -G, derivatives, prodrugs, esters and/or salts thereof as well as mixtures containing more than one of the above.

In addition, the invention envisages the use of a cyclosporin in combination with another therapeutically or propylactically active entity.

The composition may, for example by combined with another active pharmaceutical in a single oral dosage form.

Other immunosuppressants could be considered, either alone or in combination with cyclosporin or derivatives thereof. These include, but are not limited to, various other calcineurin inhibitors such as but not limited to Abetimus, Deforolimus, Everolimus, Gusperimus, Pimecrolimus, Sirolimus, Tacrolimus, Temsirolimus, glucocorticosteriods; cytostatics such as Anakinra, Azathioprine, Leflunomide, Methotrexate, Mycophenolic acid, Thalidomide; antibodies such as the T-cell receptor directed anti-CD3 OKT3; the immunophilin receptor binder sirolimus; interferons; opioids; TNFα-binding proteins, including, but not limited to, infliximab, etanercept, adalimumab, cucumin and catechins; and Mycophenolate Mofetil acid which acts as a non-competitive, selective and reversible inhibitor of inosine monophosphate dehydrogenase. The above list include derivatives thereof, including those modified to include a conjugated NO donor.

Certain natural extracts, including Neem oil, aloe vera, tripala, tumeric and other essential oils, including the omega polyunsaturated oils such as EPA, DHA, conjugated linoeic acid (CLA) and other derivatives thereof, have potential as treatments to alleviate or prevent inflammatory bowel disease as well as other intestinal disorders, including gastric, duodenal and intestinal ulcers. Additionally, certain plant extracts, including berry extracts such as blueberry, achi, resorcinolic/phenolic lipids, resveratrol, flavanoids and derivatives thereof, alone or in combination, have potential application in IBD and IBS and other intestinal or systems conditions. The mode of action of berry extracts, such as blueberry extract, remains uncertain but has effect on intestinal motility, stool formation and colonic flora. Yet other potential therapeutics include, but are not limited to, proteins, therapeutic peptides, vaccines, antibodies or fragments thereof. Local delivery to the mucosa will overcome degradation and ensure that a high local concentration is available to enhance therapeutic efficacy. Encapsulating any of the above, alone or in any combination, into minicapsules or minispheres and targeting the release to areas of the intestine that are diseased provide for enhanced disease management as well as perhaps a reduction in any potential for systemic side effects.

The invention also includes methods of treating inflammatory bowel disease comprising administering to a subject in need thereof a pharmaceutical composition comprising a dose of a cyclosporin or pharmaceutically acceptable salts, esters and pro-drugs thereof, including various salts and enantiomers thereof or covalent or non-covalent modified active or inactive entities, including nitric oxide donors (NO-donors) and at least one pharmaceutically acceptable excipient. Such formulations are preferentially developed to ensure release in the ileum and/or colon.

The invention also provides methods of treating inflammatory bowel disease comprising administering to a subject in need thereof a pharmaceutical composition comprising cyclosporin and a curcuminoid, such as, but not limited to, curcumin, with release of same targeted to the ileum or colon.

The invention also includes non-covalent complexion of a cyclosporin with a carrier such as cyclodextrins, maltodextrins, dextrins or modifications thereof and targeting the release of such to the specific sites along the gastrointestinal tract.

One more embodiment of the present invention is the inclusion of targeted gastrointestinal release of formulations containing live or live attenuated organisms, including bacteria or genetically modified bacteria and/or live or live-attenuated viruses.

In the invention, in the development of cyclosporin-based combination treatments for inflammatory bowel disease, the non-cyclospoine-based active pharmaceutical ingredient is interchangeable, including any one or combination of tacrolimus, sirolimus, hydralazine, DMOG, proply- and/or asparaginyl hydroylase inhibitors, EPA, DHA, natural plant extracts, natural marine extracts or other biological and active entities, which may include siRNA constructs.

In the invention, in the development of cyclosporin-based combination treatments for Graft-Versus-Host Disease, the non-cyclospoine-based active pharmaceutical ingredient is interchangeable, including any one or combination of tacrolimus, sirolimus, EPA, DHA, natural plant extracts, natural marine extracts or other biological and active entities, which may include siRNA constructs.

In the invention, the immunological modulating entities, including antigens, adjuvants, emulsions, oils, and small molecules are interchangeable and may be utilised for the development of vaccines, oral tolerance modulators and allergen modulators, which may include siRNA constructs.

The invention allows for the development of solid-, semi-solid or liquid-filled minicapsules comprising one or more layer and produced using conventional seamless minicapsule processes, modified melt extrusion, non-pareil coating, non-pareil drug layering or other processes that enable the production of the desired dosage form.

The result is modified release compositions that in operation deliver one or more active ingredients in a unique, bimodal or multimodal manner. The present invention further relates to solid oral dosage forms, sachets or suppositories containing such multiple minicapsule or minisphere controlled release compositions as well as methods for delivering one or more active ingredients to a patient in a bimodal or multimodal manner. Furthermore, the invention permits targeted release of orally delivered formulations to specific regions of the gastrointestinal tract to maximize absorption, confer protection on the payload, to optimize treatment of diseased intestinal tissue or enhance oral bioavailability. Additionally, the invention enables one or more pharmaceutical active to be administered sequentially or concomitantly to improve disease treatment and management and to benefit from the body's natural circadian rhythms. The invention also permits the release of pharmaceutical actives into the ileum and colon for the enhanced treatment of local intestinal diseases or to facilitate the absorption of active pharmaceutical agents, including biopharmaceuticals such as peptide and proteins.

The formulations may include the following therapeutics: steroids (e.g., budesonide and other corticosteroids, and adrenal steroids such as prednisone and hydrocortisone, administered alone or in combination with a xanthine or methylxanthine compound such as theophylline); cytokines such as interleukin-10; antibiotics; immunomodulating agents such as azathioprine, 6-mercaptopurine, methotrexate, and anti-tumor necrosis factor (TNF) agents such as soluble TNF receptor and antibodies raised to TNF; and also antinflammatory agents such as zinc are widely prescribed. The most commonly prescribed agents for IBD include sulfasalazine (salicyl-azo-sulfapyridine, or "SASP") and related 5-aminosalicylic acid ("5-ASA") products are commonly prescribed and due to significant side-effects of some of these as well as the above mentioned therapies would benefit from targeted colonic delivery and in some cases, pre-formulated to enhance solubility or permeability.

The invention may also be used to deliver live organisms, including various bacteria such as probiotics, to specific regions of the intestine or colon where they exert protective or therapeutic effects. Steidler et al (Science 2000; 289:1352-5) have shown that it is possible to first develop genetically modified bacteria to produce proteins and then to target the release of such proteins, including anti-inflammatory cytokines to regions of the gastrointestinal tract where they will optimally exert protective or therapeutic effects. The bacteria may be formulated for storage stability and target the release of such agents to the site of optimal action.

The invention further provides a multiple minicapsule modified release composition comprising at least two populations of different active ingredient-containing minicapsules in which the two or more actives are released concomitantly.

Alternatively, the invention provides a multiple minicapsule modified release composition comprising at least two populations of different active ingredient-containing minicapsules in which the two or more actives are released sequentially.

The invention is not limited to the embodiments herein before described which may be varied in detail.

The invention claimed is:

1. An oral cyclosporin composition comprising multiple minicapsules or minispheres in a single-unit dosage form, the minicapsules or minispheres having a core comprising a cyclosporin in a solubilised liquid form, and wherein the cyclosporin in a solubilised form is encapsulated with a gelling agent selected from gelatin and alginate, the minicapsules or minispheres being coated with a composition comprising ethylcellulose and having a release profile to delay release of the solubilised cyclosporin and to release the solubilised cyclosporin at least in the colon.

2. The composition of claim 1, wherein the minicapsules and minispheres are seamless.

3. The composition of claim 1, wherein the minicapsule or minisphere is a coated one layer minicapsule or minisphere.

4. The composition of claim 1 which has a dissolution profile, when tested in a U.S.P. Type II apparatus (paddles) at 37° C. and 50 rpm, in pH 6.8 buffer as follows: up to 4 hours: less than or equal to about 20% cyclosporin released; 6 hours: less than or equal to about 35% cyclosporin released; 8 hours: less than or equal to about 50% cyclosporin released; 12 hours: less than or equal to about 60% cyclosporin released; 18 hours: less than or equal to about 75% cyclosporin released; and 24 hours: from about 25% to about 100% cyclosporin released.

5. The composition of claim 1 which has a dissolution profile, when tested in a U.S.P. Type II apparatus (paddles) at 37° C. and 50 rpm, in pH 6.8 buffer as follows: 1 hour: less than or equal to about 20% cyclosporin released; 4 hours: less than or equal to about 35% cyclosporin released; 6 hours: less than or equal to about 50% cyclosporin released; 12 hours: less than or equal to about 60% cyclosporin released; 16 hours: less than or equal to about 75% cyclosporin released; and 24 hours: from about 25% to about 100% cyclosporin released.

6. The composition of claim 1 wherein the coating further contains a methacrylate.

7. The composition of claim 1, wherein the coating includes a dissolution enhancing agent.

8. The composition of claim 6 wherein the dissolution enhancing agent is degraded by bacteria normally present in the lower gastrointestinal tract.

9. The composition of claim 6 wherein the dissolution enhancing agent is selected from one or more of pectin, amylose and alginate and derivatives thereof.

10. The composition of claim 7 wherein the dissolution enhancing agent is pectin.

11. The composition as claimed in claim 6 wherein the polymeric material is ethylcellulose and wherein the coating further includes a dissolution enhancing agent, which dissolution agent is present in an amount of from 0.5 to 2% w/w of ethylcellulose.

12. The composition of claim 1 wherein each minicapsule has applied thereto a coating comprising:
 a polymeric material selected from; ethylcellulose; and a composite of methacrylate and ethylcellulose; and
 an agent degraded by bacteria normally present in the lower gastrointestinal tract.

13. The composition of claim 12 wherein the agent is selected from one or more of pectin, amylose and alginate and derivatives thereof.

14. The composition of claim 1 wherein the coating composition further comprises a natural polysaccharide.

15. The composition of claim 14 wherein the coating comprises a said coating that comprises a combination of a polymer with a natural polysaccharide and wherein the natural polysaccharide comprises a natural polysaccharide selected from amylose, pectin, alginate, amylopectin, chitosan and galactomannan.

16. The composition of claim 1, wherein the cyclosporin is cyclosporin A.

17. The composition of claim 1 wherein the core is a hydrophobic solution and the minicapsules comprise an encapsulating shell obtainable by gelling a shell solution which is gelatin-based.

18. The composition of claim 1 wherein the composition comprises minicapsules, which minicapsules have the characteristics of minicapsules obtained by utilisation of surface tensions of a hydrophobic core solution comprising the cyclosporin in a solubilised form and a shell solution that is gelatin or alginate based, which solutions are ejected through a nozzle having one orifice and subject to specific frequencies and which form into a spherical form and fall into a cooling air flow or a cooling or hardening solution where the shell solution is gelled or solidified.

19. The composition of claim 18 wherein the shell solution is gelatin-based and each minicapsule has thereon:
 a coating comprising a first polymeric material selected from; ethylcellulose; and a composite of methacrylate and ethylcellulose; and
 an optional separate coating comprising a second polymeric material.

20. The composition of claim 1 comprising a hard gelatin capsule, a sprinkle, or a tablet containing the minicapsules.

21. The composition of claim 1 wherein the cyclosporin is combined with another active pharmaceutical in a single oral dosage form.

22. A composition of claim 21 wherein the other active is selected from calcineurin inhibitors; cytostatics; antibodies and fragments thereof; sirolimus; interferons; opioids; TNFα-binding proteins; mycophenolate mofetil acid; essential oils; plant extracts; therapeutic peptides; vaccines; antibodies or fragments thereof.

23. The composition of claim 21 wherein the other active is selected from any one or combination of tacrolimus, sirolimus, hydralazine, DMOG and other prolyl- and/or asparaginyl-hydroxylase inhibitors, EPA, DHA, natural plant extracts, natural marine extracts, and siRNA constructs.

24. The composition of claim 1 wherein the cyclosporin is combined with another active pharmaceutical in a single oral dosage form, the other active pharmaceutical being selected from prolyl- and/or asparaginyl-hydroxylase inhibitors.

25. The composition of claim 1 wherein the cyclosporin is combined with hydralazine in a single oral dosage form.

26. A composition of claim 21 wherein the other active ingredient is selected from budesonide and other corticosteroids, prednisone, hydrocortisone and other adrenal steroids, administered alone or in combination with a xanthine or methylxanthine; interleukin-10 and other cytokines; antibiotics; azathioprine; 6-mercaptopurine; methotrexate and other immunomodulating agents, and soluble TNF receptor, antibodies raised to TNF and other anti-tumor necrosis factor (TNF) agents; and zinc.

27. An oral cyclosporin formulation comprising a cyclosporin and at least one pharmaceutically acceptable excipient and adapted to inhibit absorption of the cyclosporin in the upper gastrointestinal tract and to release cyclosporin in the ileum and/or colon, wherein the formulation is selected from:
 formulations in a single-unit dosage form comprising multiple solid-, semi-solid or liquid filled seamless minicapsules comprising one or more layers, the minicapsules being coated with a composition comprising ethylcellulose and having a release profile to release the cyclosporin in the ileum and/or colon, the cyclosporin being encapsulated with a gelling agent selected from gelatin and alginate; and formulations in a single-unit dosage form comprising multiple minispheres comprising (i) a hydrophobic solution or suspension comprising cyclosporin and (ii) gelatin in which the hydrophobic solution is encapsulated, the minispheres being coated with a composition comprising ethylcellulose and having a release profile to release the cyclosporin in the ileum and/or colon.

28. An oral cyclosporin composition comprising multiple minicapsules in a single-unit dosage form, the minicapsules having a core comprising a cyclosporin in a solubilised form, the minicapsules being coated with a delayed release composition comprising ethylcellulose and having a release profile to release the cyclosporin in a solubilised form in the distal gut, wherein the minicapsules are minicapsules in which the cyclosporin is encapsulated with a gelling agent selected from gelatin and alginate.

29. The composition of claim 1, wherein the minicapsules or minispheres have a release profile to release the solubilized cyclosporin in the ileum and colon.

30. The composition of claim 1, wherein the cyclosporin is protected from absorption in the upper gastrointestinal tract.

31. The composition of claim 1, wherein the minicapsules or minispheres have a release profile to release in the colon an amount of the solubilized cyclosporin effective for managing an inflammatory or immune disorder that affects the colon.

32. The composition of claim 18, wherein the cyclosporin is protected from absorption in the upper gastrointestinal tract.

33. The composition of claim 18, wherein the minicapsules have a release profile to release in the colon an amount of the solubilized cyclosporin effective for managing an inflammatory or immune disorder that affects the colon.

34. The composition of claim 33, wherein the shell solution is gelatin-based and each minicapsule has applied thereto a coating comprising a polymeric material selected from; ethylcellulose; and a composite of methacrylate and ethylcellulose.

35. The composition of claim 34, wherein the polymeric material is ethylcellulose.

36. The formulation of claim 27, wherein the minicapsules and minispheres have a release profile to release in the colon an amount of the solubilized cyclosporin effective for managing an inflammatory or immune disorder that affects the colon.

37. The composition of claim 1 which has a dissolution profile, when tested in a U.S.P. Type II apparatus (paddles) at 37° C. and 50 rpm, in pH 6.8 buffer as follows: up to 4 hours: less than or equal to about 20% cyclosporin released.

38. The composition of claim 37 which has a dissolution profile, when tested in a U.S.P. Type II apparatus (paddles) at 37° C. and 50 rpm, in pH 6.8 buffer as follows: 24 hours: from about 75% to about 100% cyclosporin released.

39. The composition of claim 1 which has a dissolution profile, when tested in a U.S.P. Type II apparatus (paddles) at 37° C. and 50 rpm, in pH 6.8 buffer as follows: 1 hour: less than or equal to about 20% cyclosporin released; 4 hours: less than or equal to about 35% cyclosporin released.

40. The composition of claim 39 which has a dissolution profile, when tested in a U.S.P. Type II apparatus (paddles) at 37° C. and 50 rpm, in pH 6.8 buffer as follows: 16 hours: about 75% cyclosporin released.

41. The composition of claim 18 which has a dissolution profile, when tested in a U.S.P. Type II apparatus (paddles) at 37° C. and 50 rpm, in pH 6.8 buffer as follows: up to 4 hours: less than or equal to about 20% cyclosporin released.

42. The composition of claim 41 which has a dissolution profile, when tested in a U.S.P. Type II apparatus (paddles) at 37° C. and 50 rpm, in pH 6.8 buffer as follows: 24 hours: from about 75% to about 100% cyclosporin released.

43. The composition of claim 18 which has a dissolution profile, when tested in a U.S.P. Type II apparatus (paddles) at 37° C. and 50 rpm, in pH 6.8 buffer as follows: 1 hour: less than or equal to about 20% cyclosporin released; 4 hours: less than or equal to about 35% cyclosporin released.

44. The composition of claim 43 which has a dissolution profile, when tested in a U.S.P. Type II apparatus (paddles) at 37° C. and 50 rpm, in pH 6.8 buffer as follows: 16 hours: about 75% cyclosporin released.

* * * * *